United States Patent
Zamora et al.

(10) Patent No.: US 6,921,811 B2
(45) Date of Patent: *Jul. 26, 2005

(54) BIOACTIVE COATING COMPOSITION AND METHODS

(75) Inventors: Paul O. Zamora, Gaithersburg, MD (US); Ray Tsang, Salt Lake City, UT (US); Shigemasa Osaki, Sandy, UT (US)

(73) Assignee: BioSurface Engineering Technologies, Inc., College Park, MD (US)

( * ) Notice: Subject to any disclaimer, the term of this patent is extended or adjusted under 35 U.S.C. 154(b) by 130 days.

This patent is subject to a terminal disclaimer.

(21) Appl. No.: 10/450,309

(22) PCT Filed: Jul. 31, 2001

(86) PCT No.: PCT/US01/24000

§ 371 (c)(1),
(2), (4) Date: Jan. 28, 2003

(87) PCT Pub. No.: WO02/10221

PCT Pub. Date: Feb. 7, 2002

(65) Prior Publication Data

US 2004/0161442 A1 Aug. 19, 2004

Related U.S. Application Data

(63) Continuation-in-part of application No. 09/629,059, filed on Jul. 31, 2000, now Pat. No. 6,342,591, which is a continuation-in-part of application No. 09/399,199, filed on Sep. 20, 1999, now Pat. No. 6,596,699, which is a continuation of application No. 09/159,276, filed on Sep. 22, 1998, now Pat. No. 5,955,588.

(51) Int. Cl.[7] .................. C08B 37/10; A61K 31/727; B05D 5/08; A61L 27/34

(52) U.S. Cl. ............. 536/21; 514/56; 523/122; 427/2.1; 427/2.13; 604/57; 623/1.42

(58) Field of Search ................. 536/21; 514/56; 523/122; 427/2.1, 2.13; 604/57; 623/1.42

(56) References Cited

U.S. PATENT DOCUMENTS

| | | |
|---|---|---|
| 5,308,617 A | 5/1994 | Halluin |
| 5,334,379 A | 8/1994 | Pillai et al. |
| 5,955,588 A | 9/1999 | Tsang et al. |

*Primary Examiner*—James O. Wilson
*Assistant Examiner*—Leigh C. Maier
(74) *Attorney, Agent, or Firm*—Stephen A. Slusher; Peacock Myers & Adams, P.C.

(57) ABSTRACT

The present invention provides a bioactive coating composition, method and devices for bodily fluid-contacting surfaces. The coating comprises a complex of Formula II: wherein $R_1$ is an $C_{1-18}$alkyl or $C_{6-32}$aryl group, each $R_2$ is independently selected from the group consisting of $C_{1-18}$alkyl and $C_{6-32}$aryl, $R_3$ is N or O, n is a number from 1 to 10, and x in a number from 1 to about 30, directly bound to a heparin-activity molecule via covalent bonding, with one or more bioactive molecules bound to the heparin-activity molecule. The bioactive molecule may be an adhesive molecule such as fibronectin, a growth factor such as basic fibroblast growth factor, or any other bioactive molecule that binds, by any mechanism, to a heparin-activity molecule (II)

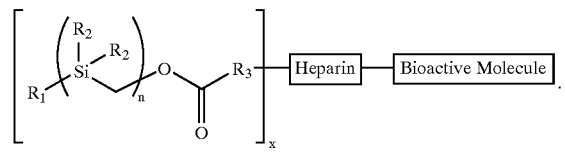

29 Claims, 8 Drawing Sheets

BIOACTIVE COATING COMPOSITION AND METHODS

CROSS-REFERENCE TO RELATED APPLICATIONS

This application is a continuation-in-part application of application Ser. No. 09/629,059 filed Jul. 31, 2000 now U.S. Pat. No. 6,342,591, issued Jan. 29, 2002, entitled Amphipathic Coating for Modulating Cellular Adhesion Composition and Methods, to Paul O. Zamora, Ray Tsang and Shigemasa Osaki, which is a continuation-in-part application of application Ser. No. 09/399,199 filed Sep. 20, 1999, now U.S. Pat. No. 6,596,699, issued Jul. 22, 2003, entitled Non-Thrombogenic Coating Compositions and Methods for Using Same, to Ray Tsang and Shigemasa Osaki, which is a continuation of application Ser. No. 09/159,276 filed Sep. 22, 1998, now patent application of U.S. Pat. No. 5,955,588, entitled Non-Thrombogenic Coating Compositions and Methods for Using Same, to Ray Tsang and Shigemasa Osaki, and the specification of each of the foregoing is incorporated herein by reference.

BACKGROUND OF THE INVENTION

1. Field of the Invention (Technical Field)

The present invention relates to coatings, methods of use of coating compositions, and coated contacting surfaces of medical devices, wherein the coating includes silyl-heparin with one or more bioactive molecules bound to the heparin, which bioactive molecules include adhesive molecules, such as fibronectin for promoting cellular attachment, growth factor molecules, such as basic fibroblast growth factor for promoting cellular growth, and a variety of other therapeutic molecules for effecting one or more therapeutic purposes.

2. Background Art

Note that the following discussion refers to a number of publications by author(s) and year of publication, and that due to recent publication dates certain publications are not to be considered as prior art vis-a-vis the present invention. Discussion of such publications herein is given for more complete background and is not to be construed as an admission that such publications are prior art for patentability determination purposes.

Heparin is naturally present in various tissues, including liver and lung, as well as the luminal surface of endothelial cells. It is composed of repeating units of D-glucuronic acid and D-glucosamine, both sulfated, in a 1,4-α linkage. Heparin is an anticoagulant, and it has been reported that on the surface of endothelial cells it minimizes fibrin accumulation. When administered as a parenteral drug, heparin activates anti-thrombin III, which leads to inactivation of thrombin and ultimately systemic inhibition of fibrin formation.

A number of medical devices that come in contact with blood have been coated with heparin with the goal of taking advantage of its thrombo-resistant nature. Stents, catheters, oxygenator fibers, and cardiac bypass circuits are examples of medical devices that have been coated with heparin (Niimi et al., *Anesth Analg* 89:573–9, 1999; Inui et al., *Artif Organs*, 23:1107–12, 1999). Various strategies have been developed to attach heparin to medical polymer surfaces including chemical conjugation (Siefert et al., *J Biomater Sci Polym Ed*, 7:277–87, 1995), plasma glow discharge methods (Kim et al., *Biomaterials*, 21:121–30, 2000), the combination of both, and hydrophobic interaction as described herein (U.S. Pat. No. 5,955,588).

Heparin has a number of other biological actions related to its similarity to heparan sulfate. In the extracellular matrix, heparin and its chemical relative heparan sulfate is complexed into a scaffolding onto which cells attach. Heparin also binds to fibronectin and other adhesive molecules. In addition, extracellular matrix heparan sulfate and heparin also act as reservoirs for growth factors, not only binding growth factors but also protecting them from protease degradation. Fibroblast growth factor (FGF), platelet-derived growth factor (PDGF), and bone morphogenic protein (BMP) are examples of growth factors that complex to heparin.

The ability of heparin to bind adhesive molecules and growth factors has lead to a number of efforts to use heparin complexes to improve implantable medical device surfaces by providing surfaces to which cells can attach and migrate. Other researchers have explored direct coatings of fibronectin, and peptides and peptide mimetics derived from fibronectin, with the goal of increasing cell attachment (Walluscheck et al., *Eur J Vasc Endovasc Surg*, 12:321–30, 1996; Boxus et al., *J Bioorg Med Chem*, 6:1577–95, 1998; Tweden et al., *J. Heart Valve Dis*, 4 Suppl 1:S90–7, 1995). Vascular grafts, for example, would be improved by a surface that supports the growth of endothelial cells. Current vascular grafts of polytetrafluoroethylene and polyethylene terephthalate do not support endothelization, and consequently patients must be maintained on long-term antplatelet therapy.

Fibronectins function as adhesive, ligand molecules interacting with specific receptors on the cell surface. Cells types that attach to fibronectin include fibroblasts, endothelial cells, smooth muscle cells, osteoblasts, and chondrocytes.

Other investigators have used heparin and fibronectin complexes to provide cell adhesion to polymeric surfaces. For example, heparin-albumin conjugates have been immobilized on carbon dioxide gas plasma-treated polystyrene (Bos et al., *J. Biomed Mater Res*, 47:279–91, 1999) and complexed to fibronectin. The fibronectin on these surfaces increased the attachment of endothelial cells. Bos et al. (*Tissue Eng* 4:267–79, 1998) reported that endothelial cells grew to confluency on $CO_2$ gas plasma-treated polystyrene coated with an albumin-heparin conjugate. ishihara et al. (*J Biomed Mater Res*, 50: 144–152, 2000) reported that a heparin-conjugated polystyrene promoted cell attachment of fibroblasts, smooth muscle cell and endothelial cells. The fibroblasts grown on heparin-conjugated polystyrene had growth rates at least comparable to fibronectin-coated, gelatin-coated, or tissue culture-treated media.

A simple method of efficiently complexing fibronectin, other adhesive molecules, growth factor molecules, and therapeutic molecules, including derivatives or mimics of the foregoing, to a heparin complex would have wide applicability for attaching cells to prostheses, including vascular grafts, bone and cartilage Implants, nerve guides and the like. Particularly needed is a method and composition permitting use of a wide variety of adhesive molecules, including fibronectin, laminin and the like, and growth factor molecules, including FGF, as part of a coating for implantable medical devices.

There further remains a need in the art for coating compositions for implantable medical devices that promote cellular attachment, and further wherein cellular attachment can be modulated by the quantity of adhesive molecule, and which can be applied simply and easily with no specialized equipment or techniques.

A primary object of the present invention is to provide a coating composition for contacting surfaces of implantable medical devices, wherein the composition comprises a silylheparin-bioactive molecule complex, attached to the contacting surface by hydrophobic interaction.

A further object of the invention is to provide an amphipathic silyl-heparin-fibronectin coating composition for contacting surfaces of implantable medical devices, which promotes cellular attachment.

A further object of the invention is to provide a coating the composition of which can be varied, such that absent an adhesive molecule the coating inhibits fibrin deposition, but when the coating includes an adhesive molecule, the coating promotes cellular attachment and cell growth.

A further object of the invention is to provide a coating the composition of which can be varied, such that in one embodiment the invention provides a silyl-heparin-growth factor molecule composition, and in another embodiment the invention provides a silyl-heparin-therapeutic molecule composition.

A further object of the invention is to provide coating compositions utilizing fibronectin, derivations of fibronectin, peptide mimics of fibronectin, laminin, vitronectin, thrombospondin, gelatin, collagen and subtypes thereof, gelatin, polylysine, polyornithine, and other adhesive molecules or derivatives or mimics of other adhesive molecules.

A further object of the invention is to provide coating compositions utilizing fibroblast growth factor, platelet-derived growth factor, vascular endothelial growth factor, hepatocyte growth factor, placental growth factor, insulin-like growth factor, nerve growth factors and neurotrophins, heparin-binding epidermal growth factor, transforming growth factor-β, bone morphogenetic protein 2, osteogenic protein 1 and keratinocyte growth factor, and other growth factor molecules or derivatives or mimics of other growth factor molecules.

A further object of the present invention is to provide a cost effective and commercially feasible method for coating polymeric medical devices, including biodegradable medical devices, with a coating comprising a bioactive molecule.

A further object of the present invention is to provide a cost effective and commercially feasible method for coating polymeric medical devices, including biodegradable medical devices, with a coating comprising a silyl-heparin-bioactive molecule composition.

A primary advantage of the present invention is that it provides for coating contacting surfaces of medical devices of complex geometries and surfaces with a durable and low-cost coating that promotes the desired biological or therapeutic effect, depending on the bioactive molecule selected.

Another advantage of the present invention is that it provides a method for determining the disassociation rate of silyl-heparin-bioactive molecule complexes from contacting surfaces by, in part, determining the number or silyl units per silyl moiety, or the number of silyl moieties per heparin molecule, or both.

Other objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated into and form a part of the specification, illustrate several embodiments of the present invention and, together with the description, serve to explain the principles of the invention. The drawings are only for the purpose of illustrating a preferred embodiment of the invention and are not to be construed as limiting the invention. In the drawings.

DESCRIPTION OF THE PREFERRED EMBODIMENTS

Figure 1:
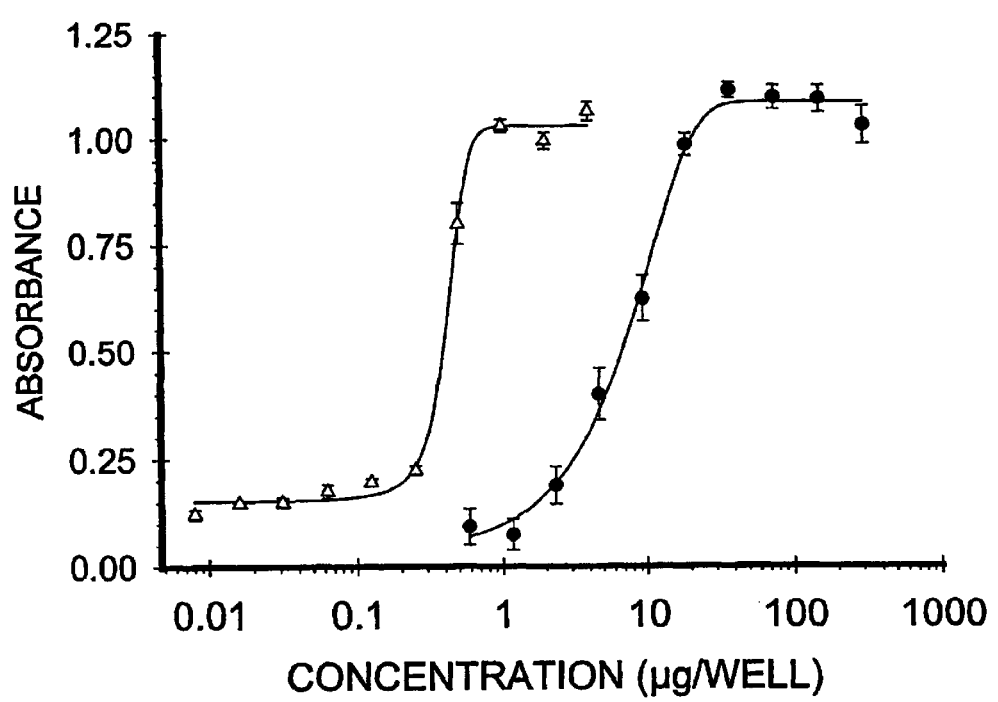
FIG. 1 is a titration plot of the amount of fibronectin and silyl-heparin needed to support cell attachment.

Best Modes for Carrying Out the Invention

The present invention relates to bioactive coating compositions comprising a silyl-heparin-bioactive molecule complex, methods for making and using the same, and devices including the same. The silyl comprises a hydrophobic silyl moiety of Formula I:

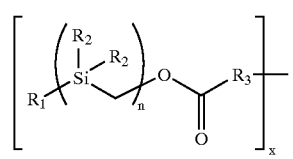

wherein $R_1$ is an $C_{1-18}$ alkyl or $C_{6-32}$ aryl group, each $R_2$ is independently selected from the group consisting of $C_{1-18}$ alkyl and $C_{6-32}$ aryl, $R_3$ is N or O, and n is a number from 1 to 10. X is from 1 to about 30, such that from 1 to about 30 silyl moieties are covalently bound to a heparin molecule. One or more bioactive molecules, which may be the same or different, are bound to the heparin molecule.

In one embodiment, the present invention provides bioactive molecules that are adhesive molecules, thereby forming an amphiphatic coating that resists fibrin accumulation and promotes cell attachment. In another embodiment, the present invention provides for bioactive molecules that are growth factors molecules, thereby forming a coating providing for regional or localized delivery of the growth factor molecules. In yet another embodiment, the present invention provides for bioactive molecules that are therapeutic molecules, thereby forming a coating providing for regional or localized delivery of the therapeutic molecules.

In another embodiment, the present invention provides medical devices with the contacting surface thereof coated with moieties of Formula I, which moieties are covalently bonded to a heparin molecule, with one or more bioactive molecules bound to the heparin molecule. The invention further includes medical devices coated with moieties of Formula I, which moieties are covalently bonded to a heparin molecule, but without a bioactive molecule bound to the heparin, wherein the coating inhibits fibrin accumulation and cellular adhesion.

In another embodiment, the present invention provides a fibrin-resistant medical device that promotes surface cellular adhesion within the body, the device having surfaces for contacting blood, cells, tissues, or other fluids. The blood- or cell-contacting surfaces have coated thereon a coating composition including the moieties of Formula I, which moieties are covalently bonded to a heparin molecule, with an adhesive molecule, including but not limited to fibronectin, complexed by affinity interaction to the heparin.

In another aspect, the invention provides a complex of Formula II:

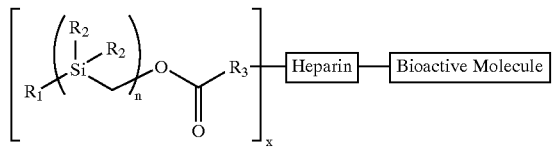

wherein $R_1$ is an $C_{1-18}$ alkyl or $C_{6-32}$ aryl group, each $R_2$ is independently selected from the group consisting of $C_{1-18}$ alkyl and $C_{6-32}$ aryl, $R_3$ is N or O, n is a number from 1 to 10, and x is a number from 1 to about 30.

These and other aspects of the present invention are described further in the description and examples of the invention which follow.

Unless otherwise defined, all technical and scientific terms employed herein have their conventional meaning in the art. As used herein, the following terms have the meanings ascribed to them.

"Alkyl" refers to linear branched or cyclic, saturated or unsaturated $C_{1-18}$ hydrocarbons such as methyl, ethyl, ethenyl, propyl, propenyl, iso-propyl, butyl, iso-butyl, t-butyl, pentyl, cyclopentyl, hexyl, cyclohexyl, octyl, and the like.

"Aryl" refers to unsaturated $C_{6-32}$ hydrocarbon rings that may be substituted from 1–5 times with alkyl, halo, or other aryl groups. Aryl also includes bicyclic aryl groups. Specific examples of aryl groups include but are not limited to phenyl, benzyl, dimethyl phenyl, tolyl, methyl benzyl, dimethyl benzyl, trimethyl phenyl, ethyl phenyl, ethyl benzyl, and the like.

"Adhesive molecule" refers to molecules which promote cellular attachment, adhesion or growth, including fibronectin, laminin, vitronectin, thrombospondin, heparin-binding domains, and heparan sulfate binding domains, as well as synthetic polymers of amino acids containing adhesive sequences derived from any of the foregoing. This includes, without limitation, peptides or polypeptides containing the amino acids with the single letter codes RGD, IKVAV (SEQ ID NO:1), YIGSR (SEQ ID NO:2), and the like. Adhesive molecules also include lectins that bind to heparin and carbohydrate moieties on cell surfaces.

"Bioactive molecule" refers to any molecule with biological activity within the body, including molecules used as a drug, to effect a biochemical change in an organism, or to confer a benefit to an organism. The bioactive molecule preferably binds to one or more forms of heparin. A bioactive molecule includes an adhesive molecule, a growth factor molecule and a therapeutic molecule as disclosed herein. A bioactive molecule further includes art conventional drugs, compounds, molecules, peptides, peptidomimetics, antibodies and fragments and mimics thereof, and the like. A bioactive molecule may, but need not, bind to a receptor in the organism, be a receptor for an endogenous substance found in an organism, or be an agonist, antagonist, or a mixed agonist-antagonist of a receptor-mediated process or reaction. In a preferred embodiment, the bioactive molecule may be bound to heparin by any means known in the art, including but not limited to affinity binding.

"Growth factor molecule" refers to any growth factor, mimic of a growth factor, derivative of a growth factor, or other molecule that has the effect of a growth factor. This includes fibroblast growth factor, platelet-derived growth factor, vascular endothelial growth factor, hepatocyte growth factor, placental growth factor, insulin-like growth factor, nerve growth factors and neurotrophins, heparin-binding epidermal growth factor, transforming growth factor-β, bone morphogenetic protein 2 (BMP-2), osteogenic protein 1 (OP-1, also called BMP-7) and keratinocyte growth factor. It further includes peptides, peptidomimetics and other molecules, whether made by synthetic means, recombinant means or otherwise, which have the biological activity of a growth factor, including without limitation any of the foregoing. In a preferred embodiment, the bioactive molecule may be bound to heparin by any means known in the art, including but not limited to affinity binding.

"Heparin" as used herein includes complex carbohydrates or mimetics of complex carbohydrates with properties similar to those of heparin, including heparan sulfate, hyaluronic acid, dextran, dextran sulfate, chondroitin sulfate, dermatan sulfate, and the like, including but not limited to a molecules including a mixture of variably sulfated polysaccharide chains composed of repeating units of D-glucosamine and either L-iduronic or D-glucuronic acids, salts of any of the foregoing and derivatives of any of the foregoing.

"Therapeutic molecule" refers to any molecule having a therapeutic effect, such as a chemokine, hormone, angiogenesis inhibitor or drug, and particularly a therapeutic molecule intended for local or regional delivery within the body over a sustained period. Examples of chemokines and modulators of the immune system include C-X-C chemokines, interferon gamma, macrophage inflammatory protein-1, interleukins, such as IL-1, IL-2, IL-3, IL-4, IL-6, IL-7 and IL-8, interferon-gamma inducible protein-10, RANTES, HIV-tat-transactivating factors, and granulocye/macrophage-colony stimulating factor. Examples of angiogenisis inhibitors include platelet factor-4 (PF-4), C-X-C chemokines lacking the ELR motif (ELR-C-X-C chemokines), endostatin and angiostatin. Examples of drugs include amino glycoside antibiotics, including streptomycin, gentimicin and neomycin B; and anti-cancer antibiotics, including actinomycin D, daunorubicin, doxorubicin, bleomycin, rapamycin and paclitaxol. In a preferred embodiment, the therapeutic molecule may be bound to heparin by any means known in the art, including but not limited to affinity binding.

In the following discussion and examples, "$\mu L$" means microliter, "mL" means milliliter; "L" means liter, "$\mu g$" means microgram, "mg" means milligram, "g" means gram, "mol" means moles, "M" means molar concentration, "Me" means methyl; "Bn" means benzyl, "$nBu_4NI$" means tetrabutyl-ammonium iodide, "° C." means degrees Centigrade. All percentages are in percent by weight unless otherwise indicated.

Silyl-Heparin Compositions

The silyl-heparin compositions of the present invention include a covalent complex of one or more hydrophobic silyl moieties with heparin. Heparin is a mixture of variably sulfated polysaccharide chains composed of repeating units of D-glucosamine and either L-iduronic or D-glucuronic acids.

Any suitable form of heparin may be employed in the reaction. A variety of salts of heparin and heparin derivatives are known in the art. For example, conventional salts of heparin include sodium heparin, calcium heparin, magnesium heparin, and potassium heparin. Heparin derivatives include, but are not limited to ammonium heparin, benzalkonium heparin, and the like. Sodium heparin is a preferred form of heparin for preparing the covalent complexes according to the present invention. All of the foregoing are included within the definition of "heparin" given above, together with salts and derivatives thereof.

The silyl moiety is represented by Formula I wherein $R_1$ is an $C_{1-18}$ alkyl or $C_{6-32}$ aryl group, each $R_2$ is independently selected from the group consisting of $C_{1-18}$ alkyl and $C_{6-32}$ aryl, $R_3$ is N or O, and n is a number from 1 to 10. As will be apparent to those skilled in the art, $R_3$ is an N or O atom in the heparin molecule, and the unoccupied bond from $R_3$ signifies the attachment of the silyl moiety to the heparin molecule. Thus, the hydrophobic silyl moiety is capable of attachment to the heparin molecule at either an O atom of an alcohol (i.e., hydroxyl) or an N atom of an amine.

Heparin comprises many repeating units containing amine and hydroxyl functional groups which can be the site for attachment of the hydrophobic silyl moiety to the heparin molecule. Accordingly, one embodiment of the present invention contemplates the attachment of more than 1 hydrophobic silyl moiety to a single heparin molecule. As many as 30 or more hydrophobic silyl moieties of Formula I, and as few as 1 hydrophobic silyl moiety, may be attached to a single heparin molecule to achieve the covalent complex employed in the heparin coating compositions of the present invention. In one embodiment of the present invention, between 2 and 25 hydrophobic silyl moieties are attached to a single heparin molecule. In another embodiment, between 5 and 20 hydrophobic silyl moieties are attached to a single heparin molecule. In another embodiment, between 7 and 15 hydrophobic silyl moieties are attached to a single heparin molecule. In a preferred embodiment, 7 or 8 hydrophobic silyl moieties are attached to a single heparin molecule. In another preferred embodiment 12 hydrophobic silyl moieties are attached to a single heparin molecule.

As disclosed herein, the silyl-heparin complex is bound to the contacting surface of a medical device by means of hydrophobic interaction between the hydrophobic silyl moiety and the contacting surface, which is preferably also hydrophobic. The strength of the attachment, and the disassociation rate of silyl-heparin complexes from the contacting surface, is determined by at least three factors: the number of silyl units per silyl moiety (i.e., where n is a number between 1 and 10), the number of silyl moieties per single heparin molecule (i.e., where x is a number between 1 and about 30), and the degree of hydrophobicity of the contacting surface. For applications where minimal or functionally no disassociation is desired, such as certain applications with adhesive molecules bound to the silyl-heparin complex, the number of silyl units per silyl moiety and the number of silyl moieties per heparin molecule may each be increased to the optimal number for maximal binding strength, and similarly the contacting surface may be selected so as to provide optimal hydrophobic binding with the silyl moieties. For applications where controlled release over time is desired, such as certain applications with growth factor or therapeutic molecules bound to the silyl-heparin complex, fewer silyl units per silyl moiety or fewer silyl moieties per heparin molecule, or both, are selected, or a contacting surface providing decreased hydrophobic binding to the silyl moiety is selected, or a combination thereof, such that the desired release over time in vivo is obtained.

In those embodiments wherein more than one hydrophobic silyl moiety is attached to a single heparin molecule, the hydrophobic silyl moieties may be attached either through the amine of heparin (e.g., where $R_3$ is N) or through the hydroxyl group of heparin (e.g., wherein $R_3$ is O). In other words, some of they hydrophobic silyl moieties may be attached to the heparin molecule via bonding at the amine groups of heparin, while other hydrophobic silyl moieties are attached to the heparin molecule via bonding at the hydroxyl groups of heparin. It is also possible for all of the hydrophobic silyl moieties to be consistently attached to heparin via one or the other of the amine (e.g., $R_3$ in all hydrophobic silyl moieties is N) or the alcohol (e.g., $R_3$ in all hydrophobic silyl moieties is O).

The bonds between the hydrophobic silyl moieties and the heparin molecule that effect the attachment of the silyl moieties to the heparin molecule are covalent bonds. Thus, the coating compositions of the present invention do not rely upon ionic interactions between heparin and the hydrophobic moiety. Rather, the hydrophobic moieties are bonded to the heparin molecule by covalent bonding through either the amine or hydroxyl groups (or possibly a combination of both amine and hydroxyl groups when two or more hydrophobic silyl moieties are attached a single heparin molecule). Because the hydrophobic silyl moiety is bound to the heparin molecule through covalent bonding, the present invention overcomes one weakness of conventionally known heparin coatings. Specifically, the problem of heparin leaching from the coating as a result of the breaking of the ionic bond between heparin and the group which attaches heparin to the surface is overcome by avoiding reliance upon ionic bonding interactions between heparin and the binding group. In the present invention, the covalent bonds between the hydrophobic silyl moieties and the heparin molecule in the coating composition are not disrupted by the presence of ionic species in the blood with which the coated surface will come into contact. The data demonstrate that this process of covalent modification also does not lead to detrimental loss of heparin activity as monitored by a Factor Xa/antithrombin III chromogenic substrate assay on the surface of target substrates.

The covalent complex according to the present invention can be prepared according to the following Scheme 1.

Scheme 1

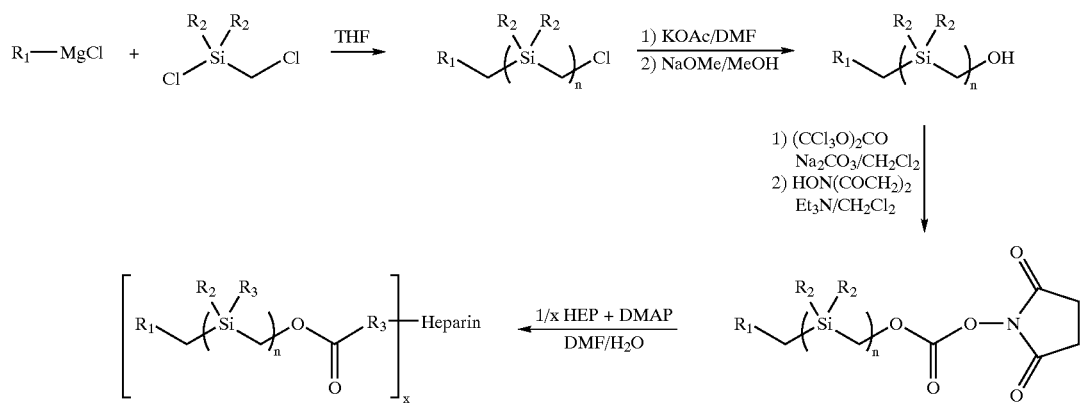

wherein $R_1$ is an $C_{1-18}$ alkyl or $C_{6-32}$ aryl group, each $R_2$ is independently selected from the group consisting of $C_{1-18}$ alkyl and $C_{6-32}$ aryl, $R_3$ is N or O, n is a number from 1 to 10, and x is a number from 1 to about 30.

Generally, the first intermediate, $R_1(Si(R_2)_2CH_2)_nCl$, wherein n is 1, is produced by reacting an alkyl or aryl magnesium chloride with a chloro(chloromethyl)-dialkyl silane or chloro(chloromethyl)diaryl silane in the presence of tetrahydrofuran (THF). The alkyl or aryl magnesium chlorides used as starting materials are commercially available, and include, for example benzyl magnesium chloride. Chloro(chloromethyl)dialkyl silanes and chloro(chloromethyl)diaryl silanes are commercially available and include, for example chloro(chloromethyl)dimethyl silane. The reaction is exothermic, and is typically conducted at temperatures of about 10° C. or less. The reaction is carried out for a sufficient period of time to yield about 80–90% product. Typically the reaction is conducted over a period of from about 2 to about 24 hours.

First intermediates wherein n is 2 or higher can be produced using a Grignard reaction involving the reaction of the first intermediate wherein n is 1 with $ClSi(R_2)_2CH_2Cl$. This Grignard reaction can be repeated any number of times to achieve the desired value for n in the first intermediate. The reaction is carried out in the presence of a catalytic amount of iodine and THF.

The first intermediate (wherein n is 1–10) is converted to the second intermediate, $R_1(Si(R_2)_2CH_2)_nOH$, by reacting the first intermediate with potassium acetate (KOAc) in dimethyl formamide (DMF), at a temperature of above about 120° C., and preferably about 135° C., for between 12 and 24 hours. The product of this reaction is then reacted with sodium methoxide (NaOMe) in methanol (MeOH) under reflux for about 2 hours to achieve the second intermediate.

The second intermediate is converted to the last intermediate, $R_1(Si(R_2)_2CH_2)_nOCO_2N(COCH_2)_2$, by a two-step reaction process. In the first step, the second intermediate is reacted with triphosgene and sodium carbonate in methylene chloride at a temperature of less than 10° C., and preferably about 0° C. The product of this reaction is reacted with N-hydroxysuccinimide and triethylamine ($Et_3N$) in methylene chloride at a temperature of less than 10° C., and preferably about 0° C.

The final intermediate is covalently conjugated to heparin by reacting heparin with the final intermediate in a suitable solvent (e.g., water/dimethyl formamide) at a pH of about 8.0 to 9.0, and preferably about 8.5. The pH of the reaction is controlled by the addition of base such as sodium hydroxide, as needed. Alternatively and preferably, a slight excess of 4-dimethylaminopyridine (DMAP) can be used as base for the conjugation reaction with heparin. Using these general methods, the covalent silyl-heparin complexes of the present invention can be produced. The covalent complexes have the general Formula III:

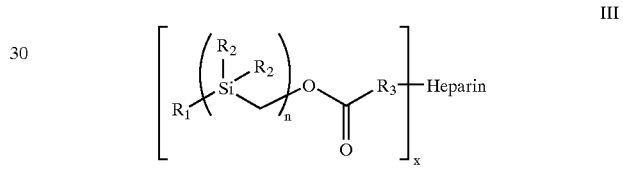

III wherein $R_1$ is an $C_{1-18}$ alkyl or $C_{6-32}$ aryl group, each $R_2$ is independently selected from the group consisting of $C_{1-18}$ alkyl and $C_{6-32}$ aryl, $R_3$ is N or O of heparin, n is a number from 1 to 10, and x is a number from 1 to about 30.

Preferred complexes include those complexes wherein $R_1$ of the hydrophobic silyl moiety is aryl. In one preferred embodiment, $R_1$ is benzyl. In one preferred embodiment, each $R_2$ is alkyl. In one particularly preferred embodiment, each $R_2$ is selected from the group consisting of methyl, ethyl, propyl, and isopropyl, particularly methyl. In one preferred embodiment, n is a number from 2 to 3.

Specific examples of covalent complexes according to the present invention include but are not limited to [benzyl-bis(dimethylsilylmethyl)]-(N-heparinyl)-carbamate, [benzyl-tris(dimethylsilylmethyl)]-(N-heparinyl)carbamate, and dodecyl[benzyl-bis(dimethylsilylmethyl)]-(N-heparinyl)-carbamate. Although these three specific covalent complexes are examples of currently preferred covalent complexes having the general Formula III above, other specific examples of such complexes will be apparent to those skilled in the art and are contemplated by the instant invention.

The silyl-heparin coatings of the present invention include the silyl-heparin covalent complexes described above. In addition to the silyl-heparin covalent complex, the coating composition may also include one or more solvents that facilitate the processes of applying the composition to the surface. Suitable solvents include those which at least partially solubilize the covalent complex and which do not interfere with the anti-thrombogenic activity of heparin. Examples of solvents which may be employed in the coating compositions of the present invention include but are not limited to aqueous solvents, alcohols, nitriles, amides, esters, ketones, ethers, and the like. "Aqueous", with reference to solutions or solvents, refers to solutions or solvents that consist primarily of water, normally greater than 90% water by weight, and includes essentially or substantially pure water. For example, an aqueous solution or solvent can be distilled water, tap water, or the like. However, an aqueous solution or solvent can also include water having substances such as pH buffers, pH adjusters, organic and inorganic salts, alcohols (e.g., ethanol), sugars, amino acids, or surfactants incorporated therein. The aqueous solution or solvent may also be a mixture of water and minor amounts of one or more co-solvents, including agronomically suitable organic co-solvents, which are miscible therewith, or may form an emulsion therewith. Examples of suitable alcohol solvents include but are not limited to methanol, ethanol, propanol, isopropanol, hexanol, as well as glycols such as ethylene glycol and the like. Examples of suitable nitriles include acetonitrile, propionitrile, butyronitrile, benzonitrile and the like. Examples of suitable amides include formamide, N,N-dimethylformamide, N,N-dimethylacetamide and the like. Examples of suitable esters include methyl acetate, ethyl acetate and the like. Examples of suitable ketones include acetone, methyl ethyl ketone, diethyl ketone and the like. Examples of suitable ethers include diethyl ether, tetrahydrofuran, dioxane, dimethoxyethane and the like. Any two or more of any of the foregoing solvents may be utilized in the coating composition as well. Currently preferred solvents include water, particularly distilled water, isopropanol, acetonitrile, and combinations of any two or more of these solvents.

In one preferred embodiment, the silyl-heparin covalent complex is solubilized in solvent to achieve a concentration of between about 0.01 and about 10 percent by weight, preferably between about 0.1 and about 1 percent, and more preferably about 0.125 percent.

In addition to the foregoing solvents, the silyl-heparin coating compositions of the present invention may also include therein various conventional additives. Examples of additives which may be incorporated into the compositions of the present invention include but are not limited to benzalkonium, 4-dimethylaminopyridinium, tetrabutylammonium halides, and the like.

Contacting Surfaces of Medical Devices

The coatings may be applied to any of a wide variety of contacting surfaces of medical devices. Contacting surfaces include, but are not limited to, surfaces that are intended to contact blood, cells or other bodily fluids or tissues of a mammal, including specifically a human. Suitable contacting surfaces include one or more surfaces of medical devices that are intended to contact blood or other tissues. The medical devices include sutures, graft materials, wound dressings, wound coverings, bone waxes, bone prostheses, aneurysm coils, embolization particles, microbeads, stents, catheters, shunts, grafts, artificial blood vessels, nerve-growth guides, artificial heart valves, prosthetics, pacemaker leads, in-dwelling catheters, cardiovascular grafts, bone replacement, wound healing devices, cartilage replacement devices, urinary tract replacements, orthopedic implants, opthalmic implants and other medical devices known in the art. Other examples of medical devices that would benefit from the application of the present invention will be readily apparent to those skilled in the art of surgical and medical procedures and are therefore contemplated by the instant invention. The contacting surface may include a mesh, coil, wire, inflatable balloon, or any other structure which is capable of being implanted at a target location, including intravascular locations, intralumenal locations, locations within solid tissue, and the like. The implantable device can be intended for permanent or temporary implantation. Such devices may be delivered by or incorporated into intravascular and other medical catheters.

Suitable contacting surfaces include metals such as stainless steel, nitinol, titanium, tungsten, platinum, graphite and metal alloys; ceramics; any of a variety of polymeric materials such as polyvinyl chloride, polyethylene, polylactide, polyglycolide, polycaprolactone, polymethyl methacrylate, polyhydroxylethyl methacrylate, polyurethane, polystyrene, polycarbonate, dacron, polytetrafluoroethylene and extended polytetrafluoroethylene (Teflon®), related fluoropolymer composites (Gore-Tex®), polyester, polypropylene, polyamide, polyacrylate polyvinyl alcohol and copolymers of any two or more of the foregoing; siloxanes such as 2,4,6,8-tetramethylcyclotetrasiloxane; natural and artificial rubbers; and glass. In general, the contacting surface that may be coated with a silyl-heparin-bioactive molecule of the present invention includes any surface that has an affinity or attraction to the hydrophobic silyl moiety. Such surfaces are typically hydrophobic surfaces.

In one embodiment, the contacting surface may be a biodegradable or bioerodible material. Biodegradable or bioerodible materials are known in the art, and include polyanhydrides, polyglycolic acid, polylactic/polyglycolic acid copolymers, polyhydroxybutyrate-valerate and other aliphatic polyesters. Biodegradable implantable materials are described in U.S. Pat. Nos. 5,656,297; 5,543,158; 5,484,584; 4,897,268; 4,883,666; 4,832,686; and 3,976,071. In one embodiment, a bioabsorbable polymeric contacting surface is made from a biocompatible polymeric material such as polycaprolactone, poly(D,L-lactide), poly(L-lactide), polyglycolide, poly(dioxanone), poly(glycolide-co-trimethylene carbonate), poly(L-lactide-co-glycolide), poly(D,L-lactide-co-glycolide), poly(L-lactide-co-D,L-lactide) or poly(glycolide-co-trimethylene carbonate-co-dioxanone). In one embodiment, the persistence of the bioabsorbable polymeric structural component within a living organism is in excess of the anticipated period over which the bioactive agent will provide a therapeutic effect, and is preferably in excess of at least two such periods.

Application of Silyl-Heparin Complex

The silyl-heparin complex may be coated onto any of the contacting surfaces as set forth above. Any suitable method for applying the silyl-heparin complex to the surface may be employed. One suitable method for applying the silyl-heparin complex to the contacting surface is by dipping the contacting surface into a coating composition containing the silyl-heparin complex of the present invention. A liquid coating composition containing the silyl-heparin complex of the present invention may be prepared using any of the solvents described above. The surface is dipped or immersed into a bath of the coating composition. Typically, the dipping process is carried out at elevated temperatures, such as between about 30° C. and about 80° C., and for a defined period of time, such as for a period of between about 5 and about 20 minutes, preferably about 10 minutes. Thereafter, the surface may be allowed to remain in contact with the coating composition containing the silyl-heparin complex for a period of between about 15–60 minutes, preferably about 20 minutes, at room temperature.

Another method that may be employed for coating or applying the coating compositions of the present invention onto a contacting surface includes use of pumping or spraying processes. In a pumping process, a coating composition having a concentration of between 0.05 and about 5 percent (w/v) silyl-heparin complex is pumped through that portion of a medical device including a contacting surface for about 30 minutes. Thereafter any excess coating composition may be washed out with water or saline. Similarly, the contacting surface may be coated with the coating composition by spraying.

Following coating, the resulting silyl-heparin complex coated surface is typically washed with water or other aqueous solutions prior to drying. Advantageously, the foregoing methods for applying the coating composition to a surface are relatively quick, commercially feasible and cost-effective. They require no special equipment or special technical training, and can be applied to devices with complex surface geometries. Thus the silyl-heparin complex may be applied to any contacting surface, including three-dimensional matrices, rods, coils, tubes, sheets, pins, screws, threads, braids, beads, particles, spheres and combinations thereof.

The hydrophobic interaction between the hydrophobic contacting surface and the hydrophobic silyl moieties of the silyl-heparin complex forms a bond between the silyl moiety of the silyl-heparin complex and the surface. This hydrophobic interaction is sufficiently strong so as to provide a reasonable stable bond between the covalent complex and the surface. Advantageously, and depending in part on the hydrophobicity of the material of the contacting surface, a definable disassociation rate may be obtained, such that a given percentage of silyl-heparin complexes, together with the bioactive molecule bound to heparin, disassociate from the contacting surface, thereby providing for local or regional delivery of the bioactive molecule over a period of time. Such disassociation rate may be determined, in part, by the number of silyl units per silyl moiety or the number of silyl moieties bound to each heparin molecule, or both, and accordingly such numbers are selected based, in part, on the desired disassociation rate.

Adhesive Molecule Complexation and Use

The bioactive molecule may be an adhesive molecule such as fibronectin. Fibronectin has known and demonstrated affinity for heparin. Fibronectins are composed of two similar protein chains, with each chain including one domain for cell binding and two domains, one at each end of the chain, for heparin binding. Affinity binding of fibronectin results in an affinity constant of approximately $10^8$ M/L.

Any form of fibronectin may be employed, including fibronectin derived from cells, plasma, or tissues, natural or genetically engineered, and of human origin or derived from another animal species. Other adhesive molecules, as defined above, may also be employed, utilizing the methods described herein for fibronectin.

Following coating of the contacting surface with a silyl-heparin complex, the fibronectin may be affinity complexed to the heparin, resulting in a silyl-heparin-fibronectin complex. To affinity complex the fibronectin, the fibronectin is solubilized in one or more solvents which facilitate the processes of applying the fibronectin composition to the silyl-heparin-coated contacting surface. Suitable solvents include those which at least partially solubilize fibronectin and which do not interfere with the activity of heparin or the cellular-attachment activity of fibronectin. Examples of solvents that may be employed in the present invention include aqueous solutions as defined above; aqueous solutions containing alcohols, nitriles, amides, esters, ketones, ethers, and the like; and alcohols, nitrites, amides, esters, ketones, ethers, and the like. Aqueous solutions are particularly useful for non-synthetic fibronectins and organic-based solvents are particularly useful for synthetic fibronectins and peptides derived therefrom.

The fibronectin composition can be applied to the silyl-heparin-coated contacting surface to render the contacting surface suitable for cellular adhesion and attachment. Any suitable method for applying the fibronectin composition to the surface may be employed. One suitable method for applying the fibronectin composition to the silyl-heparin-coated contacting surface is by dipping the silyl-heparin-coated contacting surface into a fibronectin composition of the present invention. The silyl-heparin-coated surface is dipped or immersed into a bath of the fibronectin solution. Typically, the dipping process is carried out at elevated temperatures, such as between about 30° C. and about 80° C., and preferably between about 40° C. and about 50° C., for a period of between about 5 and about 60 minutes, preferably between about 20 and about 30 minutes.

Other methods that may be employed for coating or applying the fibronectin solutions of the present invention on to silyl-heparin-coated surfaces include use of pumping or spraying processes. In one embodiment, the fibronectin solution has a concentration of between 0.05 and about 5 percent (w/v) fibronectin, and is pumped through that portion of a medical device including a contacting surface for about 30 minutes. Thereafter any excess coating composition may be washed out with water or saline. Similarly, the contacting surface may be coated with the coating composition by spraying.

Following attachment of the fibronectin to the heparin of the silyl-heparin complex of the composition onto the contacting surface, the contacting surface may be washed with water or saline prior to drying. Advantageously, the foregoing methods for applying the coating composition to a surface are relatively quick, commercially feasible and cost-effective.

In an alternative embodiment, the fibronectin may be complexed in an aqueous solution with silyl-heparin, and then the entire silyl-heparin-fibronectin complex attached to the contacting surface. In this embodiment, the silyl-heparin is dissolved in an aqueous solution and mixed with a predetermined amount of fibronectin, such that the fibronectin is essentially entirely complexed with the silyl-heparin. An organic solvent such as isopropanol may be added to the aqueous solution to a concentration of between 20% and 80%, and preferably about 35%. Under these conditions the silyl-heparin-fibronectin complex undergoes the formation of micelles, with the fibronectin-heparin portion of the complex sequestered on the inside of the micelle. A solution of micelles can then be applied to the surface of a contacting surface, thereby allowing the micelles to associate with such contacting surface by hydrophobic interaction. Rinsing in an aqueous solution may then be employed to remove excess unbound material and allow the heparin-fibronectin to associate in the aqueous phase. This approach may advantageously be used with, for example, fibronectin-derived peptide polymers.

In yet another embodiment, other adhesive molecules may be employed in addition to the adhesive molecules discussed above. These include, without limitation, polylysine, polyornithine, and similar molecules with net positive charges that associate with heparin by charge-charge interaction and thereby provide cell adhesive properties. Polylysine and polyornithine are known to enhance cell attachment on certain types of cell culture ware, and may be applied and bound to silyl-heparin complexes as described herein.

A variety of growth factors and cytokines can also be complexed to extracellular matrix heparin or heparan sulfate and employed as adhesive molecules. The bound growth factors can thereby be used to promote cell adhesion by providing a display of ligands to which cell surface receptors can bind. Fibroblast growth factor (FGF), platelet-derived growth factor (PDGF), and bone morphogenic protein (BMP) are examples of growth factors that complex to heparin. Similarly, cytokines are known to interact with heparin, and cytokines, such as gamma-interferon, may be bound to extracellular matrix heparin or heparan sulfate compositions of this invention, including the silyl-heparin complexes.

In yet another embodiment, more than one type of adhesive molecule may be bound to silyl-heparin complex. Thus, both a growth factor and fibronectin may be applied to the silyl-heparin complex such that the composition contains both types of adhesive molecules. For many adhesive molecules, affinity binding to heparin is through distinct receptors, such as with fibronectin and a fibroblast growth factor, for example. The bound growth factor thereby provides a mechanism to maximize cellular growth on the coated surface.

The heparin and fibronectin coating compositions of the present invention can be applied to contacting surfaces that contact blood, tissue, cells or other bodily constituents of any of a wide variety of medical devices, thereby providing the medical device with one or more contacting surfaces promoting cellular adhesion and attachment. Examples of specific medical devices which may be advantageously treated with the a silyl-heparin-adhesive molecule complex include, but are not limited to, artificial blood vessels, blood shunts, nerve-growth guides, artificial heart valves, prosthetics, pacemaker leads, in-dwelling catheters, cardiovascular grafts, bone replacements, wound healing devices, cartilage replacement devices, urinary tract replacements and the like. Other examples of medical devices which would benefit from the application of the adhesive molecule coating compositions of the present invention will be readily apparent to those skilled in the art of surgical and medical procedures and are therefore contemplated by the instant invention.

It is also possible and contemplated to use these coatings in other applications, include use for cell culture and other biological ex vivo applications wherein a surface for cellular adhesion is desired.

Growth Factor Molecule Attachment and Use

Heparin-containing delivery systems for local or regional application of growth factors have been described by several investigators. When the heparin is covalently bound to a scaffolding, the release of growth factors is understood to be related to enzymatic factors such as heparinase or plasmin, and more significantly by diffusion-based release of the growth factor from the heparin. Diffusion is, however, not favored because the complex of growth factor and heparin is stable and is rendered immobilized by the conjugation of heparin. In this invention, the silyl-heparin complex is not covalently bound to the contacting surface, but is rather bound by hydrophobic interaction. As a consequence, the complex of silyl-heparin-growth factor molecule is subject to efflux and more effective biological effect.

A growth factor molecule may be adsorbed onto the heparin surface of a silyl-heparin complex bound by hydrophobic interaction to a contacting surface of a medical device. Such adsorption may be by dipping, pumping, spraying or other means known in the art, including those discussed above with respect to adhesive molecules.

Silyl-heparin-growth factor molecules complexes were attached to suitable contacting surfaces, including polystyrene and lactide:glycolide copolymers. Immunoassays were used to establish that basic fibroblast growth factor (bFGF) readily bound to silyl-heparin complexes on a contacting surface, and that the amount of bFGF bound was directly related to amount offered for binding. Once adsorbed the silyl-heparin-bFGF was able to induce capillary tube formation of endothelial cells and to increase the growth of endothelial cells. When coated onto suture material as a contacting surface and implanted in muscle, the silyl-heparin-bFGF coating caused increased fibroblastic cellularity in the area of the implant. The devices and methods of this invention may thus be employed in a growth factor delivery system for use in tissue repair providing localized release of bFGF and related growth factors to enhance the repair process.

Fibroblast growth factors comprise a large family of developmental and physiological signaling molecules. All FGFs have a high affinity for the glycosaminoglycan heparin and for cell surface heparan sulfate (HS) proteoglycans. The affinity of FGF for heparan sulfate limits its diffusion and restricts its release into the extracellular matrix. The binding of FGFs to heparin or HS results in the formation or stabilization of dimers and higher order oligomers along the proteoglycan chain. Heparin and HS also play a role in the formation of an active FGF/FGF receptor signaling complex, and heparin and HS increase the affinity and half-life of the resulting FGF and receptor complex. bFGF is mitogenic in many cell types including fibroblasts, endothelial cells, smooth muscle cells and osteoblasts, among others. It is angiogenic and a survival factor.

Examples of medical devices with which silyl-heparin-growth factor molecule complexes may be employed include sutures, graft materials, wound dressings, wound coverings, nerve growth guides, bone waxes, aneurysm coils, embolization particles, microbeads, stents, dental implants, orthopedic implants, optholmic implants and bone prosthesis. A single silyl-heparin-growth factor molecule complex may be utilized, two or more silyl-heparin-growth factor molecule complexes may be utilized, or a silyl-heparin complex may include a growth factor molecule in combination with either an adhesive molecule or therapeutic molecule, or both. Similarly, in a single medical device more than one contacting surface may be employed, such that one contacting surface contains one or more silyl-heparin-growth factor molecule complexes, and another contacting surface contains a different silyl-heparin-growth factor molecule complex, or a silyl-heparin-adhesive molecule complex, or a silyl-heparin-therapeutic molecule complex, or a combination thereof. For example, a medical device may have one contacting surface that contacts tissue, with a silyl-heparin-adhesive molecule complex coating thereon, and another contacting surface that contacts blood, with a silyl-heparin-growth factor molecule complex or a silyl-heparin-therapeutic molecule complex coating thereon.

Disease states wherein silyl-heparin-growth factor molecule complex coatings on coating surfaces may be of particular utility include burns, cardiovascular ischemia, peripheral vascular ischemia, vascular aneurysms, bone fractures, skeletal defects, sites of orthopedic trauma, sites of cartilage damage, cancer treatment, prophylaxis of bacterial growth, neural damage, myocardial infarction, peripheral vascular occlusion, ocular degeneration, kidney ischemia and the like.

In one embodiment, a silyl-heparin-growth factor molecule complex coating is employed for use in treatment of cerebral aneurysms. Endovascular coils, such as those made from platinum, titanium, or nitinol, with a diameter of about 0.015 cm to 0.031 cm and lengths of 4 cm to 10 cm are employed. The surface of the endovascular coil is coated with a silyl-heparin-growth factor molecule complex, such as benzyl-bis(dimethylsilylmethyl) oxycarbamoyl-heparin bound by hydrophobic interaction to the contacting surface of the endovascular coil, with bFGF bound by affinity binding to the heparin. The coated endovascular coil is then deployed, such as from a catheter guided under fluorography to the aneurysm. After deployment within the cavity of the aneurysm, the coil is detached from the delivery device. The number of silyl moieties attached to each heparin molecule or the number of silyl units in each silyl moiety, or both, is selected such as to provide disassociation of the silyl-heparin-growth factor molecule complex from the coil at a determined and desired rate. This provides an improved endovascular coil with a mechanism to stimulate repair and strengthening of the aneurysm vessel wall. The mechanism involves, in part, the heparin and bFGF stimulating transient and local cell growth leading to a stronger blood vessel wall, such effect being modulated and increased by release of the silyl-heparin-bFGF complex from the endovascular coil at a determined rate.

It has been determined by use of immunoassays that both fibrinogen and bFGF can be bound to heparin on a silyl-heparin complex, without displacement of either, resulting in formation of a mixed complex of silyl-heparin and fibrinogen and bFGF. Such mixed complexes may be employed to coat endovascular coils and contacting surfaces of other medical devices. In the case of endovascular coils, the silyl-heparin-fibrinogen contributes to efficacy of thrombus formation and cellular attachment due to effect of the fibrinogen, while the silyl-heparin-bFGF contributes to cell growth.

In another embodiment, a silyl-heparin-growth factor complex coating is used on microparticles for local and transient delivery of heparin and growth factor to increase collateral blood flow and to increase angiogenesis in ischemic tissue. Microparticles are made, such as by homogenizing a methylene chloride solution containing 3% polylactide:polyglycolide (PLGA) with a 2% polyvinyl alcohol aqueous solution to form an emulsion, sonicating the resulting mixture, and recovering particles by centrifugation after evaporation of the organic phase. After evaporation of methylene chloride, the PLGA microparticles are incubated in an aqueous solution containing 0.5% silyl-heparin, such as benzyl-bis(dimethylsilylmethyl) oxycarbamoyl-heparin, for 45 minutes. Unbound silyl-heparin is removed by centrifugation and rinsing in phosphate buffered saline. The silyl-heparin coated microparticles can then be resuspended in an aqueous buffer, such as a buffer containing dextrose, and optionally aliquoted into unit doses, lyophilized, and optionally sterilized by gamma radiation. The growth factor molecule can then be incorporated immediately prior to use, by preparing growth factor molecules in an aqueous solution, such as phosphate buffered saline containing 1% human serum albumin, and adding the growth factor molecules and solution to the lyophilized silyl-heparin coated microparticles. Alternatively, the microparticles are coated with a silyl-heparin-growth factor complex, such as by coating with silyl-heparin and subsequently adding the growth factor molecule, incubating the microparticles with growth factor molecules at the desired concentration, removing unbound growth factor by centrifugation and rinsing. The silyl-heparin-growth factor molecule complex coated microparticles are then optionally lyophilized and sterilized as described above. Any of a variety of growth factors may be employed, including bFGF, transforming growth factor-$\beta$ (TGF-$\beta$) and vascular endothelial growth factor (VEGF). The silyl-heparin-growth factor is released from the microparticles over a selected period of time, such as several days, thereby providing local and transient delivery of heparin and growth factors. In one embodiment, the length of the silyl moiety may be modified, by appropriately selecting "n" in Formula I or II and accordingly synthesizing the resulting silyl moiety, thereby modifying the rate of release or disassociation from the contacting surface of the microparticle, and thus controlling bioavailability in vivo. Similarly, the number of silyl moieties per heparin molecule may be modified, by appropriately selecting "x" in Formula I or II, thereby also modifying the rate of release or disassociation from the contacting surface of the microparticle, and thus controlling bioavailability in vivo.

Therapeutic Molecule Attachment and Use

Therapeutic molecules have been used in a wide variety of drug delivery systems, methods and devices, well known in the art, for local or regional delivery of therapeutic molecules. The methods described above with respect to adhesive molecules and growth factor molecules may be employed with therapeutic molecules. In a preferred embodiment, a therapeutic molecule is selected which binds, by affinity binding or other means, to heparin, thereby resulting in formation of a silyl-heparin-therapeutic molecule complex.

INDUSTRIAL APPLICABILITY

The invention is further illustrated by the following non-limiting examples.

EXAMPLE 1

Method for Preparing Silyl-Heparin Covalent Complexes

Treatment of benzylmagnesium chloride 1 with chloro(chloromethyl)dimethysilane 2 gave benzyl(chloromethyl)dimethysilane 3 (n=1), all as shown in Scheme 2 below. Treatment of $3_n$ with magnesium gave the Grignard Reagent, which was treated with chloro(chloromethyl)dimethyl-silane again to give the homologous silyl compound $3_{n+1}$. The Grignard reaction can be repeated over and over again to obtain the desired chain-length for the silyl compound. The chloro-silyl compound 3, on treatment with potassium acetate, followed by trans-esterification of the corresponding acetate with basified methanol gave the alcohol 4. The alcohol 4, when treated with triphosgene gave the corresponding chloroformate, which on treatment with N-hydroxy-succinimide gave the N-hydroxy-succinimidyl-carbonate 5. The conjugation of heparin with 5 was achieved by treatment of heparin with 5 and 4-(dimethylamino) pyridine in 1:1 DMF/$H_2O$ to give the silylated heparin 6. Adjusting the molar ratios of the reactants controlled the number of prosthetic groups per heparin.

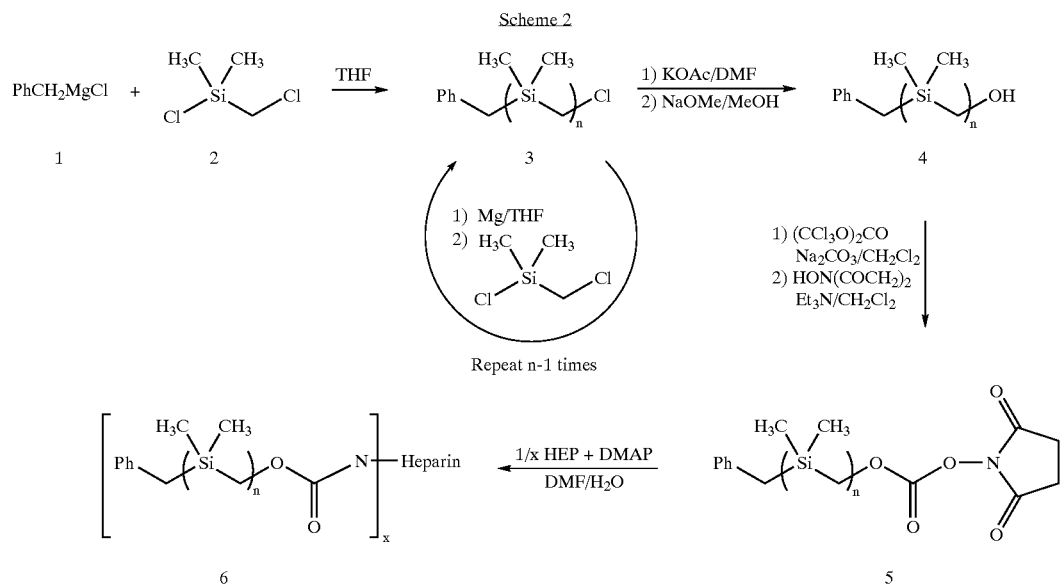

Scheme 2

Synthesis of Benzyl(chloromethyl)dimethylsilane, 3 (n=1). Under an atmosphere of nitrogen, chloro (chloromethyl)dimethylsilane (100 mL, 0.744 mol) was added by syringe to THF (500 mL) and solution cooled to 0° C. with an ice/acetone bath. Benzylmagnesium chloride (2.0 M solution, 400 mL, 0.8 mol) was added dropwise over 2 hours. Care was taken to maintain the temperature below 10° C. until all the reagent was added. Thereafter, the ice bath was allowed to warm up to room temperature and the reaction mixture stirred overnight. Hexane (300 mL) was added and saturated aqueous $NH_4Cl$ (300 mL) added dropwise. The reaction mixture was transferred to a 2 L separatory funnel with more hexane (300 mL). After partitioning, the organic layer was washed with saturated aqueous $NH_4Cl$ (200 mL) and saturated aqueous NaCl (200 mL). The combined aqueous layers were backwashed with hexane (2×500 mL) and the combined organic layers dried over $MgSO_4$, evaporated on a rotary evaporator, and further concentrated under vacuum to give a colorless oil 162.0 g (109.5% yield). A quantitative yield was assumed with a purity of the crude product being 91.3%.

Grignard Reaction of $Bn(SiMe_2CH_2)_nCl3_n$ and $ClSiMe_2CH_2Cl$ to give $Bn(SiMe_2CH_2)_{n+1}Cl$, $3_{n+1}$. Magnesium powder (7.5 g, 0.31 mol), a catalytic amount of iodine and THF (100 mL) were placed in a 500 mL 3-necked flask equipped with a condenser-$N_2$ inlet, a septum and a thermometer. The mixture was heated to reflux briefly until the brown color of iodine disappeared. $Bn(SiMe_2CH_2)_nCl$ (0.2 mol) was added by syringe and residual reagent washed into the reaction mixture with THF (2×25 mL). The reaction was initiated with a heat gun: an exothermic reaction was observed and the reaction flask was placed in a water bath until the exothermic reaction subsided. The resulting gray mixture was heated to reflux for 24 hours. The reagent was then cooled to room temperature and cannulated into a pressure filter funnel where it was added directly into another 500 mL round bottom flask in which was placed a solution of $ClSiMe_2CH_2Cl$ (27.0 mL, 0.2 mol) in THF (50 mL) at room temperature. The magnesium residue was washed into the reaction mixture with THF (2×25 mL). The reaction mixture was heated to reflux overnight. To the resulting gray suspension was added saturated aqueous $NaHCO_3$ (50 mL) and the resulting solution transferred to a 500 mL separatory funnel with hexane (200 mL). After partition, the organic layer was washed with saturated aqueous $NaHCO_3$ (50 mL) and saturated aqueous NaCl (50 mL). The combined aqueous layers were back-washed with hexane (2×100 mL), dried over $MgSO_4$, and extensively evaporated under vacuum to give an amber oil. The amber oil was purified by distillation to give colorless oil. Yields were over 80%.

Conversion of $Bn(SiMe_2CH_2)_nCl$ $3_n$ to $Bn(SiMe_2CH_2)_n$OH $4_n$-$Bn(SiMe_2CH_2)_nCl$ (0.16 mol) was dissolved in DMF (300 mL) in a 1-L 3-necked flask. KOAc (50 g, 0.5 mol) was added followed by $nBu_4Nl$ (4.0 g, 0.01 mol) and the reaction mixture was stirred in a 135° C. oil bath for 24 hours. The reaction mixture was worked up by cooling to room temperature and transferring to a 1 L separatory funnel with hexane (500 mL) and washed with saturated aqueous NaCl (3×100 mL). The combined aqueous layers was back-washed with hexane (3×300 mL) and the combined organic layers dried over $MgSO_4$ and vacuum-evaporated to an amber oil, which was dissolved in MeOH (400 mL). A generous amount of freshly prepared NaOMe was added to adjust the pH to >10 and the reaction mixture heated to reflux for 2 hours. The reaction mixture was neutralized with AcOH, evaporated to dryness and chromatographed with silica gel in a 6.5×100 cm (height of silica 40 cm) flash column and eluted with 0–30% EtOAc/hexane to give the desired product, a slightly yellow oil. Yields were over 80%.

Conversion of $Bn(SiMe_2CH_2)_nOH$ $4_n$ to $Bn(SiMe_2CH_2)_n$-$OCO_2N(COCH_2)_2$ $5_n$. Triphosgene (60 g, 0.2 mol) was dissolved in $CH_2Cl_2$ (200 mL) and stirred at 0° C. under $N_2$ in a 1-L 3-necked flask equipped with thermometer, dropping funnel and $N_2$ inlet. $Na_2CO_3$ (65 g, 0.6 mol) was added followed by $Bn(SiMe_2CH_2)_nOH$ (0.13 mol dissolved in 200 mL of $CH_2Cl_2$) dropwise over 30 minutes. Thereafter, the ice/acetone bath was allowed to come to room temperature. The reaction mixture was stirred overnight, filtered through a sintered glass funnel, and the reaction vessel rinsed with $PhCH_3$ (200 mL). The solution was concentrated under vacuum to give a colorless oil. The oil was dissolved in $CH_2Cl_2$ and stirred in an ice bath under $N_2$. N-Hydroxysuccinimide (30 g, 0.26 mol) was added followed by Et₃N (40 mL, 0.28 mol) dropwise over 15 minutes and the resulting cloudy mixture stirred at room temperature for one hour. The reaction mixture was diluted with hexane (600 mL), washed with saturated aqueous NH₄Cl (3×100 mL), and the combined aqueous phases backwashed with hexane (2×200 mL). The combined organic phases were dried over MgSO₄ and concentrated under vacuum to give amber oil. The amber oil was chromatographed on silica gel in a 6.5×100 cm (height of silica 40 cm) flash column and eluted with 20–50% EtOAc/hexane to give an amber syrup. Yields are generally greater than 75%.

Conjugation of Heparin with $Bn(SiMe_2CH_2)_nOCO_2N(COCH_2)_2$ $5_n$ to give $6_{n,x}$. Heparin (ammonium ion-free, average molecular weight 10,000; 100 g, 10 mmol) was dissolved in H₂O (500 mL) in a 2 L flask with stirring. DMF (400 mL) was added followed by DMAP (1.6×g, 13×mmol). $Bn(SiMe_2CH_2)_nO—CO_2N(COCH_2)_2$, $5_n$ (10×mmol) in DMF (100 mL) was added and the resulting milky mixture was allowed to stir at room temperature for >24 hrs. The reaction mixture was concentrated by evaporating most of the water followed by trituration with acetone (2 L). The white suspension was filtered through a sintered glass funnel to give a white solid residue. This crude material was purified by soxhlet extraction with acetone overnight to give a white powder. The yields were generally greater than 95%.

The average number of prosthetic units per molecule of heparin was estimated based on a comparison of the molar ratios of the hydrolyzed prosthetic unit benzyl-tri (dimethylsilyl-methyl)-OH and heparin as determined by use of dimethyl methylene blue. Heparin was detected using a commercially-available enzyme-linked assay that measures the heparin-induced inhibition of antithrombin/factor Xa as measured with a factor Xa specific chromogenic substrate.

EXAMPLE 2

Techniques for Applying Silyl-Heparin Coating Compositions to Surfaces

The silyl-heparin complex of Example 1 was used as a coating solution as a 1% solution (w/v) in 60% aqueous ethanol. Materials were coated with silyl-heparin for 15 minutes at 37° C. The coated materials were then were rinsed extensively in water, air-dried, and stored until use.

In another embodiment, the silyl-heparin complex was dissolved in distilled water with gentle stirring, and an organic solvent added, such as isopropyl alcohol or acetonitrile, such that the organic solvent constituted approximately ⅔ of the volume, such as 100 mg of silyl-heparin complex of Example 1 solubilized in 27 mL of distilled water with gentle stirring, with 53 mL of isopropyl alcohol or acetonitrile then added, providing a resulting concentration of the silyl-heparin complex in solution of about 0.125%. In other embodiments, the resulting solution had a silyl-heparin complex concentration of between 0.01 and 10 percent based upon the weight of the solution. The material to be coated was dipped in the solution at elevated temperatures usually ranging from 30° C. to 50° C. for about 10 minutes, followed by standing in room temperature for about 20 minutes. The coated material was taken out of the coating solution and rinsed thoroughly with distilled water or saline solution prior to drying.

EXAMPLE 3

Stability of Heparin Coating Compositions on Surfaces Exposed to Ionic Environments Various surfaces coated according to Example 2 were evaluated for heparin activity after washing with 3% (by weight) sodium chloride solution. Surface heparin activity was measured in mIU/cm² according to the technique described in Sigma Diagnostics, Heparin, Procedure No. CRS 106.

Results obtained from the evaluation of average heparin activity on various surfaces after washing with sodium chloride are set forth in Table 1 below. The concentration of the covalent complex in the coating solution was 0.25% (W/V).

TABLE 1

| Material Coated | Percent by volume of isopropyl alcohol in IPA/H₂0 solvent | | | | | |
|---|---|---|---|---|---|---|
| | 50% | 55% | 60% | 65% | 70% | 75% |
| | mIU of Heparin/Square Centimeter | | | | | |
| POLYCARBONATE | 6.8 | 8.0 | 17.6 | 16.3 | 14.7 | 14.9 |
| TMCTS | 0.4 | 3.8 | 3.5 | 2.0 | 1.1 | 2.4 |
| POLYESTER | 4.5 | 4.4 | 5.5 | 3.7 | 5.3 | |
| POLYVINYL CHLORIDE | 2.6 | 2.9 | 10.0 | 6.5 | 4.0 | 2.8 |
| STAINLESS STEEL | 12.9 | 13.1 | 8.3 | 11.0 | 12.9 | 13.8 |

EXAMPLE 4

Silyl-Heparin Application Prior to Fibronectin Attachment

Benzyl magnesium chloride was treated serially with chloro(chloromethyl) dimethylsilane to give a benzyl-(1,2 tetramethyl)disilyl compound. The benzyldisilyl compound was modified to form an activated N-hydroxy-succinimidyl carbonate that was, in turn, conjugated to heparin to form a benzyl-(1,2 dimethyl)disilyl heparin. This is shown in Scheme 3 below.

Scheme 3

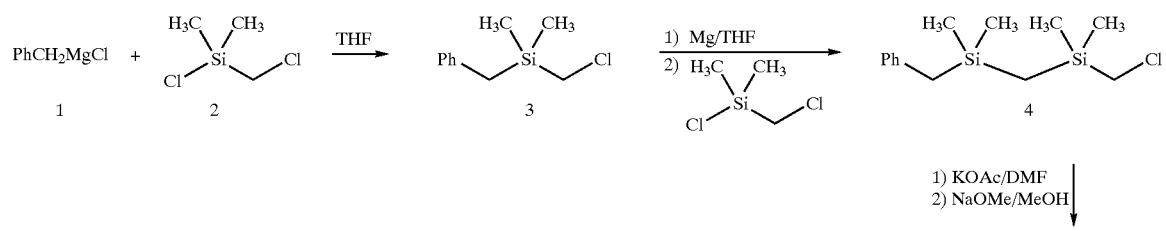

1) KOAc/DMF
2) NaOMe/MeOH

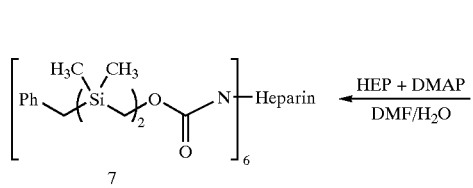 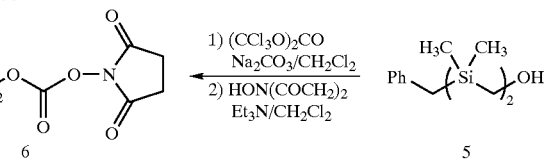

The silyl-heparin was used as a 1% solution in 70% acidified, aqueous ethanol. To coat wells, the silyl-heparin solution was applied in 20 μL/well for 15 minutes at 50–60° C. The wells were then rinsed several times in saline and air-dried. To coat contacting surfaces, the contacting surface was immersed in a 1% silyl-heparin solution for 15 minutes at 50–60° C., and rinsed extensively in water or saline.

The silyl-heparin complex may be applied to any polymeric substrate, either forming a medical or other implantable device, or coated or otherwise forming a surface of a medical or other implantable device. The complex was applied, as described, to polystyrene and polyurethane polymeric surfaces. The polymeric substrate includes biodegradable polymers, including, for example, polylactide, polylactide:polyglycolide and polycaprolactone, to which the silyl-heparin complex was applied. The silyl-heparin complex may also be applied to any metallic substrate.

EXAMPLE 5

Attachment of Fibronectin to Silyl-Heparin Coated Substrate

Fibronectin was attached to silyl-heparin coated contacting surfaces of Example 4 by incubation in an aqueous 0.9% saline solution and 20 μg/mL bovine plasma fibronectin. After 30 minutes the unbound fibronectin was removed by rinsing. The silyl-heparin-fibronectin coated contacting surfaces were then either used directly or air dried and stored for subsequent use.

EXAMPLE 6

Detection of Heparin and Fibronectin

Using contacting surfaces coated with silyl-heparin as in Example 4, and to which silyl-heparin-fibronectin was attached as in Example 5, the presence of both heparin and fibronectin was detected in analytical assays. Heparin was detected using a commercially-available an enzyme-linked assay kit (Sigma Chemical Co., St. Louis) that measured the heparin-induced inhibition of antithrombin/factor Xa as measured with a factor Xa specific chromogenic substrate. The enzyme-inhibition assay was performed in low-attachment 96 well plates following the directions of the manufacturer.

To insure that the amphipathic heparin did not introduce an unknown variable in the enzyme inhibition assay, a second assay was performed using a hydrazine-activated biotin in low-attachment 96 well plates. A solution of hydrazine-activated biotin was added to wells that were uncoated or coated with silyl-heparin complex. The solution was composed of 0.1 M sodium acetate, pH 5.2, containing 350 g of EZ-link biotin-LC-hydrazine (Pierce Chemical Co.). After 30 minutes, the wells were rinsed in water and quenched in 5% dextrose. A solution of PBS containing 20% serum and a 1:1000 dilution of horseradish peroxidase-conjugated avidin (HRPO-avidin) was added. After 30 minutes the unbound material was rinsed and a chromogenic solution of chromogen (2,2'-azinobis 3-ethylbenzothiazoline-6-sulfinic acid) (1-Step ABTS, Pierce Chemical Co.) added. Upon color development, an aliquot of 0.2 M sulfuric acid was added to stop the reaction, and the absorbance detected at 650 nm.

Fibronectin was detected immunochemically. The assays were performed in low-attachment 96 well plates in wells with no coating, a coating of fibronectin, or a coating of silyl-heparin/fibronectin. PBS containing a saturating amount of gelatin and rabbit anti-human fibronectin (known to be cross-reactive with bovine fibronectin) was added to the wells. After 30 minutes the primary antibody was removed, the plate rinsed, and a solution of PBS containing a saturating amount of gelatin and goat anti-rabbit IgG was added. After 30 minutes the unbound material was rinsed off and a chromogenic solution of ABTS (1-Step ABTS, Pierce Chemical Co.) added. Upon color development, an aliquot of 0.2 M sulfuric acid was added to stop the reaction, and the absorbance detected at 650 nm.

EXAMPLE 7

Cells Used for Adhesion Studies

Several cell types were used, including GS-9L cells (rat gliosarcoma), C3H10T1/2 (murine fibroblasts), Jurkat (human T cell), bovine aorta endothelial (BAE) cells and rat lymphocytes. GS-9L and C3H10T1/2 cells were maintained in log phase growth and detached from cultureware using Versene and collected by centrifugation. Jurkat cells grew as single cell suspensions and were collected by centrifugation. Rat lymphocytes were collected from heparinized blood by density gradient isolation over Ficoll-Hypaque® media. The collected cells were rinsed once by low speed centrifugation and suspended in either serum-free Dulbecco's Modified Eagles Medium (DMEM) containing pyruvate or RPMI 1640 containing 10% fetal bovine serum (FBS) supplemented with pyruvate. Aliquots of $10^4$ cells in 100 μL were used in subsequent adhesion studies.

The cells were examined after plating using an inverted, phase-contrast microscope. At selected time points up to 4 days after initial seeding, the cells were rinsed three times in saline and fixed in buffered 10% formalin or 35% ethanol. In some cases, the cells were stained in situ with a 0.01 % aqueous solution of crystal violet. The amount of attachment was scored visually or quantitated. To establish the relative number of cells bound, crystal violet stained cells were dissolved in a solution of 70% ethanol containing 0.1% sodium dodecyl sulfate and 0.38 M Tris and the absorbance monitored at 610 nm, using the methods of Scragg and Ferreira (*Anal Biochem* 198:80–5, 1991) and Grando et al. (*Skin Pharmacol* 6:135–47, 1993).

EXAMPLE 8

Attachment of Cells

The cells of Example 7 were added to untreated polystyrene wells, wells coated with silyl-heparin as in Example 4, with silyl-heparin-fibronectin as in Example 5, and with only fibronectin by incubation as described in Example 5. As shown in Table 2, C3H10T1/2 fibroblasts, GS-9L gliosarcoma, Jurakt T cells, bovine aorta endothelial (BAE) cells and rat lymphocytes cultured in serum-containing medium on low-attachment, nominally non-adherent polystyrene did not attach to the substrate. Similarly, these cells cultured on silyl-heparin alone did not attach. When seeded following pre-treatment with bovine fibronectin, isolated C3H10T1/2 cells and isolated GS-9L cells were found attached. When cells were cultured on silyl-heparin-fibronectin, CH310T1/2, BAE and GS-9L cells rapidly attached and spread onto the substrate. Cells were seeded at a concentration of $10^4$ cells/well in serum-containing medium.

TABLE 2

| | CELL ATTACHMENT | | | |
|---|---|---|---|---|
| CELL TYPE | UN-TREATED | SILYL-HEPARIN | FIBRO-NECTIN | SILYL-HEPARIN-FIBRO-NECTIN |
| GS-9L | – | – | +/– | ++++ |
| C3H10T1/2 | – | – | +/– | ++++ |
| BAE | – | +/– | – | +++ |
| Jurkat | – | – | – | – |
| Lymphocytes | – | – | – | +/– |

EXAMPLE 9

Adherence and Cell Spread

Using the methods as described in Example 8, GS-9L, C3H10T1/2 and BAE cells were adhered by 1 hour after seeding on silyl-heparin-fibronectin, and many of the cells demonstrated evidence of spreading onto the substrate. By 2 hours nearly all of the cells evidenced spreading. 10 The morphology of GS-9L, C3H10T1/2 and BAE cells after 24 hours on silyl-heparin-fibronectin were similar to cells grown on conventional tissue cultureware. The cells grew to confluency by 4 days. Cells seeded in serum-free medium attached and spread although not as well as in serum-containing medium, and further did not grow. No effort was made to grow the cells in a defined- or serum-low medium known to support growth. Addition of up to 10 U of heparin to the medium 15 of cells plated onto silyl-heparin-fibronectin coated plates did not inhibit the attachment or growth of C3H10T1/2. The results for GS-9L and C3H10T1/2 cells are shown in Table 3.

TABLE 3

| | CHARACTERISTIC | | |
|---|---|---|---|
| | ATTACHMENT | SPREADING | GROWTH |
| GS-9L CELLS | | | |
| Serum | ++++ | ++++ | ++++ |
| Serum-free | +++ | +++ | – |
| C3H10T1/2 CELLS | | | |
| Serum | ++++ | ++++ | ++++ |
| Serum-free | +++ | +++ | – |

EXAMPLE 10

Use on Variety of Substrates

The general applicability of silyl-heparin-fibronectin complex was evaluated by applying this coating using the methods of Examples 4 and 5 to a variety of surfaces, including polystyrene, polylactide:polyglycolide, polycaprolactone, polyurethane and stainless steel. As in Example 9 above, C3H10T1/2 cells did not attach to polystyrene. C3H10T1/2 cells also did not attach to polyurethane. They did, however, bind moderately well to polylactide:polyglycolide and to polycaprolactone, and very well to stainless steel. Regardless of the substrate, coating with silyl-heparin essentially eliminated cell attachment. The inhibition of cell attachment was noted even on surfaces known to support cell growth, such as stainless steel. Even when the cells were cultured for up to 4 days, no cell attachment was evident. Treating the plates with heparin alone did not inhibit attachment. Fibronectin alone did not significantly support cell attachment to polystyrene. It did, however, improve the attachment of cells to polyurethane and polylactide:polyglycolide, and to a lesser extent polycaprolactone. Silyl-heparin-fibronectin increased the cell density for all substrates relative to the uncoated surfaces, and increased the cell density on polycaprolactone by about 2-fold. The results are summarized in Table 4.

TABLE 4

| | C3H10T1/2 CELL ATTACHMENT | | | |
|---|---|---|---|---|
| SURFACE | UN-TREATED | SILYL-HEPARIN | FIBRO-NECTIN | SILYL-HEPARIN-FIBRO-NECTIN |
| Polystyrene | – | – | –/+ | ++++ |
| Polyurethane | – | – | ++++ | ++++ |
| Polyactide:poly-glycolide | ++ | – | ++++ | ++++ |
| Stainless steel* | ++++ | – | ++++ | ++++ |
| Polycaprolactone* | +/– | +/– | ++ | ++++ |

*determined by crystal violet staining

In related studies, heparin-specific assays and diemethylene blue dye uptake were used to establish that silyl-heparin complexes could be bound to a variety of materials including polystyrene, hydrogel-coated polystyrene, polycarbonate, polyurethane, poly caprolactone, polyvinylchloride, stainless steel and titanium. The loading efficiency of silyl-heparin complexes varied by substrate material, but was generally in the range of 10–40 mIU of heparin per $cm^2$.

EXAMPLE 11

Determination of Optimal Concentrations of Fibronectin and Silyl-Heparin

The optimal amount of fibronectin and silyl-heparin to support attachment of C3H10T1/2 cells was determined by cross-titration, as shown on FIG. 1. The $EC_{50}$ for fibronectin was approximately 0.5 μg/well and that of s-heparin about 8.7 μg/well. The cell attachment curve for the fibronectin dilution had a rapid fall-off, suggestive of a threshold effect. The fall-off for the silyl-heparin was more gradual. The curve of the relative amount of silyl-heparin on the substrate following serial dilution generally followed the cell attachment curve. The curve of the relative amount of fibronectin bound to silyl-heparin did not mirror the cell attachment curve.

In FIG. 1, fibronectin (Δ—Δ) or silyl-heparin (•—•) were titrated to determine the quantity needed to support attachment of C3H10T1/2 cells. All dilutions were performed in quadruplicate in wells of 96-well plates of low-attachment polystyrene. For titration of fibronectin, silyl-heparin was applied at 30 µg/well in 70% ethanol as in Example 4. After rinsing, fibronectin was applied in doubling dilutions of phosphate buffered saline starting from 4 µg/well. For titration of silyl-heparin, silyl-heparin was applied in doubling dilutions in 70% ethanol starting from silyl-heparin concentrations of 30 µg/well. Fibronectin was then applied in saline at 4 µg/well. Cells were at a concentration of $10^4$ cells/well in growth medium. For both experiments, the cells were allowed 24 hours to attach and then were rinsed and fixed in buffered formalin. The cells were stained for 5 minutes with 0.01% aqueous crystal violet and the absorbance at 610 nm determined.

Figure 2A:
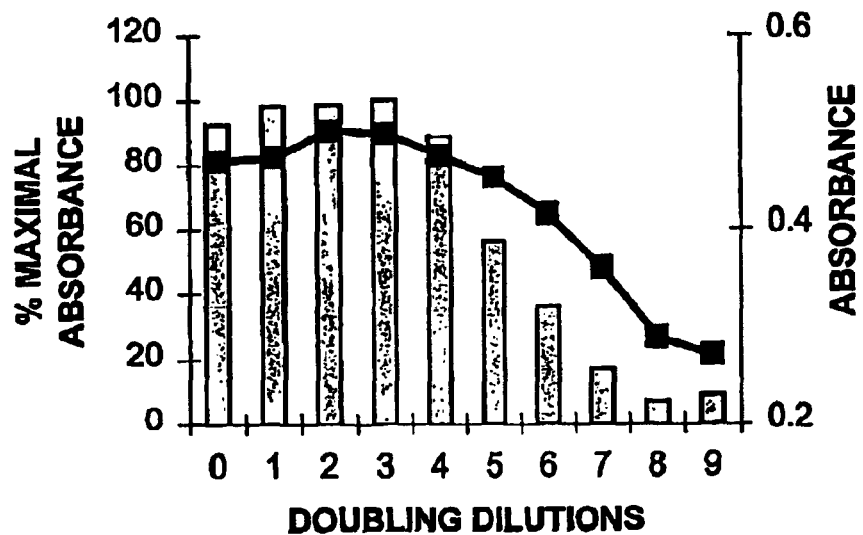
FIG. 2A and FIG. 2B depict the absorbance resulting from heparin and fibronectin added in serial doubling dilutions measured using assays.
Figure 2B:
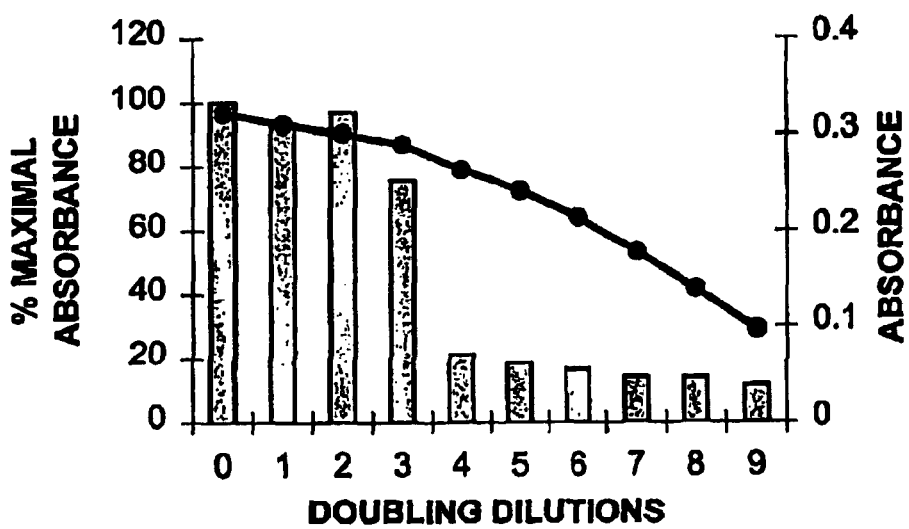

FIG. 2 shows the relative amounts of bound heparin and fibronectin in doubling dilutions to attached cell density. In FIG. 2A, the relative amount of bound heparin (■) was compared to subsequent attached cell density following complexation with fibronectin (●) (4 µg/well). In FIG. 2 B, the relative amount of bound fibronectin (FN) to wells coated with silyl-heparin (300 µg/well) was compared to subsequent cell density obtained after fibronectin complexation. Cell density was expressed as the percent maximal absorbance of crystal violet. Heparin was detected using an enzyme-linked assay while fibronectin was detected immunochemically.

EXAMPLE 12

Use of Other Adhesive Molecules

Laminin was attached to the silyl-heparin coated contacting surfaces of Example 4 by incubation in an aqueous 0.9% saline solution containing 20 µg/mL intact murine laminin. After 30 minutes the unbound laminin was removed by rinsing. In studies similar to those in Example 8, C3H10T1/2 cells attached to surfaces coated with the silyl-heparin-laminin complex.

EXAMPLE 13

Use of Different Silyl-Heparin-Adhesive Molecules

Silyl-heparin complexes were evaluated for ability to bind to several adhesion molecules as shown in Table 5. Silyl-heparin complexes bound fibrinogen and a number of other adhesion molecules including type IV collagen and fibronectin. Attachment of C3H10T1/2 cells after two hours to wells of 96-well, hydrogel-polystyrene plates coated with silyl-heparin complexes and the listed adhesive molecule was detected by staining with crystal violet. All proteins were used at a concentration of 100 µg/ml in buffered saline. Serum was used without dilution. Statistical significance was assessed relative to the values from buffered saline using Student's t-test, with * indicating p<0.05,  indicating p<0.01 and * indicating p<0.001.

TABLE 5

| Adhesive Molecule | Average ± S.E. |
| --- | --- |
| Control (saline) | 0.05 ± 0.03 |
| albumin | 0.08 ± 0.00 |
| fibrinogen | 1.63 ± 0.17** |
| fibronectin | 1.00 ± 0.10** |
| gelatin | 0.15 ± 0.05 |
| Matrigel | 1.70 ± 0.42* |
| poly-l-ornithine | 0.92 ± 0.28* |
| poly-l-lysine | 1.18 ± 0.06*** |
| serum | 0.16 ± 0.02 |

TABLE 5-continued

| Adhesive Molecule | Average ± S.E. |
| --- | --- |
| transferrin | 0.15 ± 0.03 |
| type VI collagen | 2.01 ± 0.08*** |

EXAMPLE 14

Preparation of Silyl-Heparin Complexes for Use with Growth Factor Molecules

Silyl-Heparin was prepared as generally disclosed in Example 1, with 3 silyl units per silyl moiety. The average number of silyl moieties per molecule of heparin was estimated based on a comparison of the molar ratios of the hydrolyzed prosthetic unit benzyl-tri(dimethylsilyl-methyl)-OH and heparin as determined by use of dimethyl methylene blue. Heparin was detected using a commercially-available enzyme-linked assay that measures the heparin-induced inhibition of antithrombin/factor Xa as measured with a factor Xa specific chromogenic substrate. The silyl-heparin complex was used in a coating solution at 1% solution (w/v) in 60% aqueous ethanol. Contacting surfaces were coated with silyl-heparin for 15 minutes at 37° C. The wells were rinsed extensively in water, air-dried, and stored until use.

EXAMPLE 15

FGF Binding by Silyl-Heparin Complexes and Heparin

Figure 3:
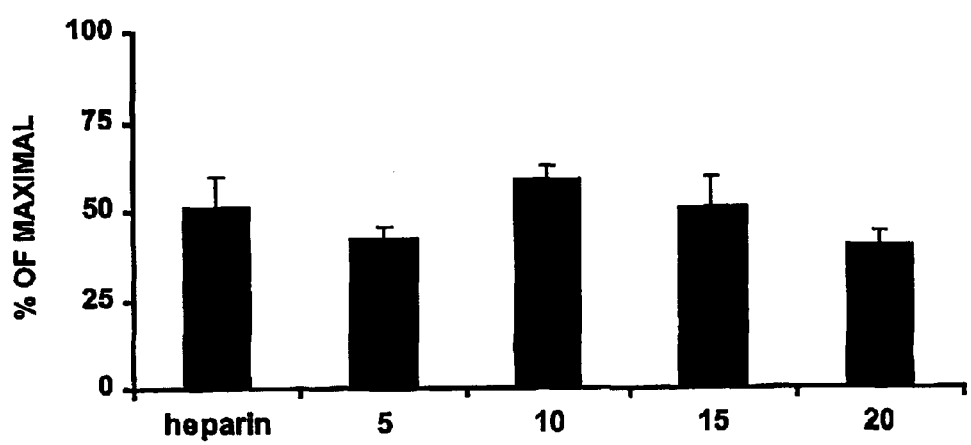
FIG. 3 depicts a comparison of the inhibition of basic fibroblast growth factor (bFGF) binding to heparin-agarose by heparin and various silyl-heparin complexes determined by immunochemical methods. The silyl moiety contained three silyl units, with between 5 and 20 silyl moieties per heparin molecule.

Binding of bFGF to heparin agarose and various silyl-heparin complexes of Example 14 were compared. Heparin agarose was rinsed in phosphate buffered saline and equilibrated in PBS containing 1% bovine serum albumin (PBS/BSA). Aliquots were added to microfuge tubes and the volume adjusted to 0.5 mL with 0.5 mL of PBS/BSA. An additional 0.5 mL of Dulbecco's modified Eagle's medium containing 10% FBS containing heparin or various silyl-heparin complexes was added. An aliquot of 5 µL of bFGF (50 ng/mL) was added and the solutions incubated for 30 minutes with mixing. The unbound bFGF was removed by multiple centrifugations and rinsing in PBS. Rabbit anti-bFGF (1:500) was added in 0.5 mL PBS/BSA and the solution incubated with mixing for 1 hour. After rinsing donkey anti-rabbit (1:500) in PBS/BSA was added and incubated 1 hour. After rinsing and transfer to new vials, chromogen (ABTS One-Step, Pierce Chemical Co.) was added and the reaction developed and subsequently read at 595 nm. The inhibition of binding of bFGF to heparin-agarose was used to compare silyl-heparin complexes with between 5 and 20 silyl moieties per heparin molecule with heparin not bound to silyl moieties. The heparin used in this assay was the same as was used in the synthesis of the silyl-heparins. As shown in FIG. 3, each silyl heparin complex composition provided essentially the same $EC_{50}$ as unmodified heparin when used on equal weight basis.

EXAMPLE 16

FGF Concentration Binding by Silyl-Heparin Complexes

Figure 4A:
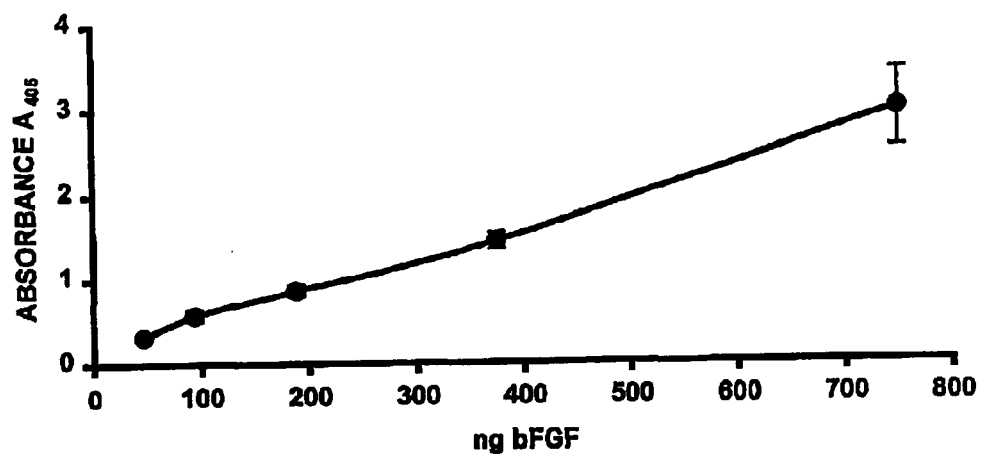
FIG. 4A and FIG. 4B are plots of the bFGF concentration on signal strength, using primary and secondary antibodies at a dilution of 1:500 (A) and at a dilution of 1:250 (B). The data represents the average ±S.D.
Figure 4B:
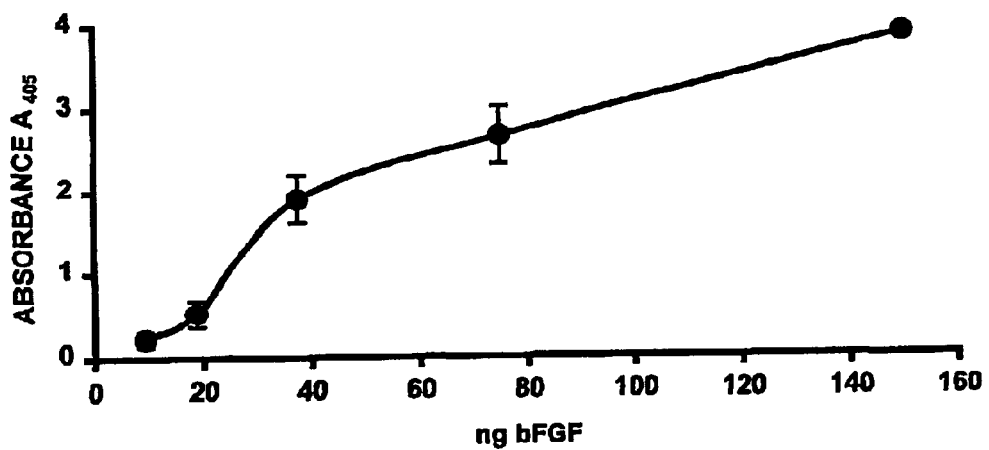

Wells of 96 well polystyrene microtiter plates, with a well surface area of 0.32 $cm^2$, were coated with 30 µl of silyl heparin for 15 minutes at 37° C. After rinsing and air-drying, bFGF (Sigma Chemical Co.) in PBS/BSA was added in 150

µL aliquots in doubling dilutions. The plate was incubated at 37° C. for 1 hour and rinsed 5 times in PBS. An aliquot 150 µl of PBS/BSA containing 1:500 rabbit anti-FGF antibodies were added, incubated for 1 hour and rinsed. In some cases an irrelevant rabbit antibody was used at a similar concentration (rabbit anti-TGF-receptor II, Santa Cruz Biotechnology). An aliquot of PBS/BSA containing 1:500 HRPO-conjugated donkey anti-rabbit IgG added, and after incubation and rinsing ABTS-chromogen added. All antibody solutions were filtered through 0.2 micron filters prior to use. The absorbance was monitored at 405 nm. As shown in FIGS. 4A and 4B, bFGF was detected over concentrations from as low as 20 ng to as high as 750 ng. Color development was linear at high concentrations, indicating that under conditions of the assay the upper saturation limit of the silyl-heparin complex for bFGF had not been reached. When anti-TGF-II (irrelevant antibody directed against the transforming growth factor receptor) was used instead of anti-FGF and at the same anti-dilutions, no bFGF was detected. When TGF-β, at a concentration of 40 ng was used as the growth factor molecule, no activity was detected with anti-bFGF antibodies.

EXAMPLE 17

Effect of Adhesive Molecules on FGF Binding

Figure 5:
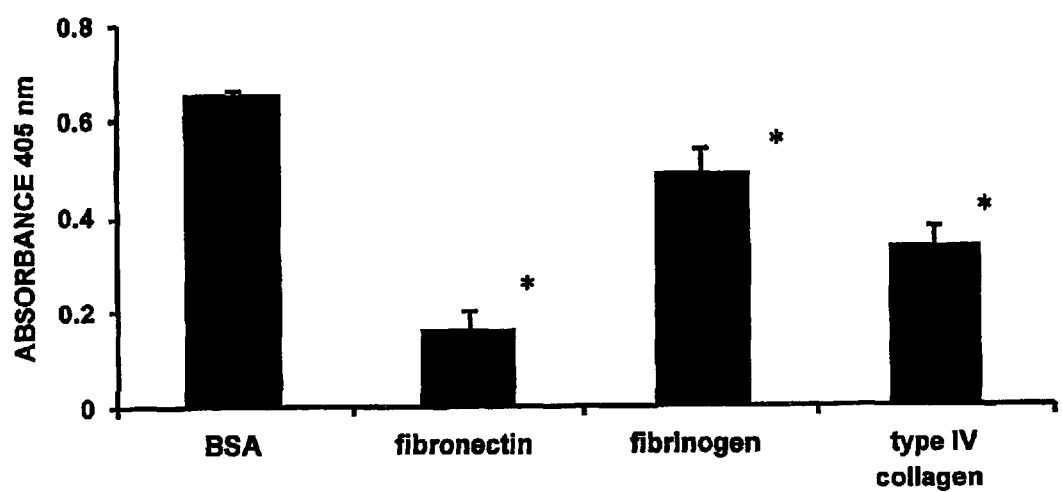
FIG. 5 is a plot depicting the effect of complexing adhesive molecules to silyl-heparin on subsequent binding of bFGF. All adhesive molecules (fibronectin, fibrinogen and type IV collagen) were complexed to silyl-heparin at a concentration of 100 μg/mL with unbound material rinsed prior to binding of bFGF. The data is the average ±S.D, with the asterisk indicating p<0.05 by Student's t-test.

Murine type IV collagen, human fibrinogen and bovine fibronectin isolated from plasma were bound to silyl-heparin complexes bound to wells of polystyrene microtiter plates, at a concentration of 100 µg/mL in PBS/BSA. 100 µL of a selected adhesive molecule was added to each well, with incubation for 1 hour at 37° C. After extensive washing, bFGF in PBS/BSA in 150 µL aliquots was added to each well. The plate was incubated at 37° C. for 1 hour and assayed as in Example 16 using dilutions of 1:200 and 1:500 for the primary and secondary antibody, respectively. As shown in FIG. 5, fibronectin significantly decreased the binding of bFGF to the silyl-heparin-adhesive molecule complex, with less significant decrease in binding with type IV collagen and fibrinogen.

EXAMPLE 18

Capillary Tube Formation Using Silyl-Heparin-Growth Factor Complexes

Low attachment 96 well plates were coated with saline, silyl-heparin complex, silyl-heparin-fibrinogen complex or silyl-heparin-bFGF complex. Bovine aorta endothelial cells ($5 \times 10^3$ cells) were seeded into each well in DMEM containing 10% FBS. The cells were allowed to grow for 4 days and the cultures examined by phase contrast microscopy. Bovine aorta endothelial cells underwent morphological changes consistent with the formation of capillary tube formation when cultured on a contacting surface coated with silyl-heparin-fibrinogen-bFGF. Tubes did not form when the cells were cultured in wells coated with silyl-heparin, silyl-heparin-fibrinogen, fibrinogen, fibrinogen and bFGF, or bFGF. On tubes coated with silyl-heparin-fibrinogen the cells formed essentially confluent monolayers.

EXAMPLE 19

Silyl-Heparin-FGF Complex Disassociation and Biological Activity

Figure 6:
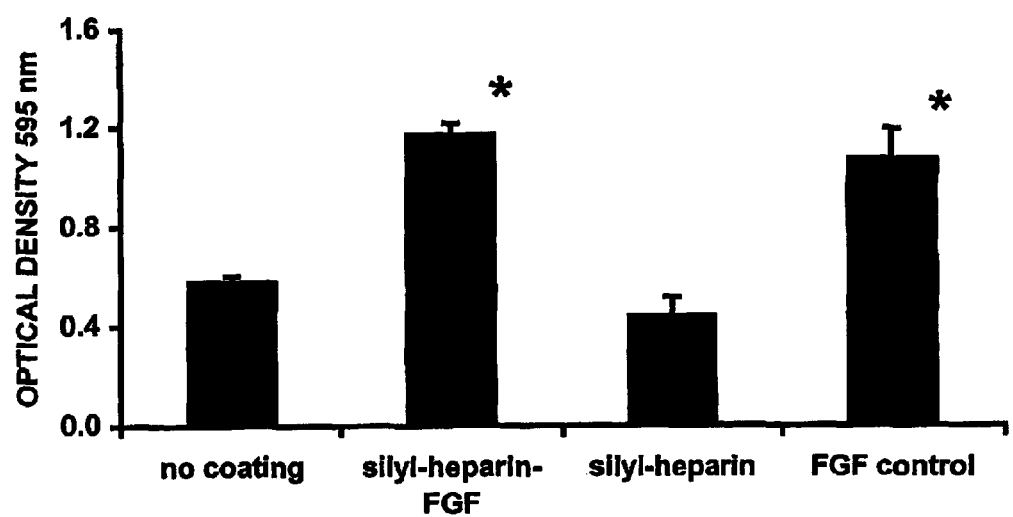
FIG. 6 is a plot depicting the effect of FGF-silyl-heparin from coated sutures across a porous membrane on the growth of bovine aorta endothelial cells after 4 days as determined by crystal violet staining. Data is the average absorbance ±S.D., with the asterisk indicating p<0.05 by Student's t-test.

Six-well cluster plates were seeded with $5 \times 10^4$ bovine aorta endothelial cells. Cell culture insert membranes (25 mm diameter) with 3 micron pores in the bottom were placed in each well. Suture material was coated with silyl-heparin-bFGF or silyl-heparin. 10 cm of suture material, either coated or uncoated, was placed in each well and medium added sufficient to cover the suture (3 mL total). One set of inserts containing an uncoated suture was spiked with 50 ng of bFGF by adding the bFGF directly to the medium and was used as a positive control. The cells were allowed to grow for 4 days, and were then fixed and stained with crystal violet. Thereafter, the stain was eluted in aqueous methanol and 0.4% SDS and monitored at 595 nm. bFGF from the silyl-heparin-bFGF coated suture was able to transit the separating permeable 3 micron membrane and act regionally to stimulate the growth of endothelial cells at the end of 4 days, as shown in FIG. 6. The cell numbers increased in wells containing suture material coated with silyl-heparin-bFGF complex and separated by the membrane to a similar extent as observed in control cultures spiked with soluble bFGF. Suture material coated with only silyl-heparin complex did not result in an increase in cell number.

EXAMPLE 20

Sutures Coated with Silyl-Heparin-bFGF Implanted in Muscle

Figure 7:
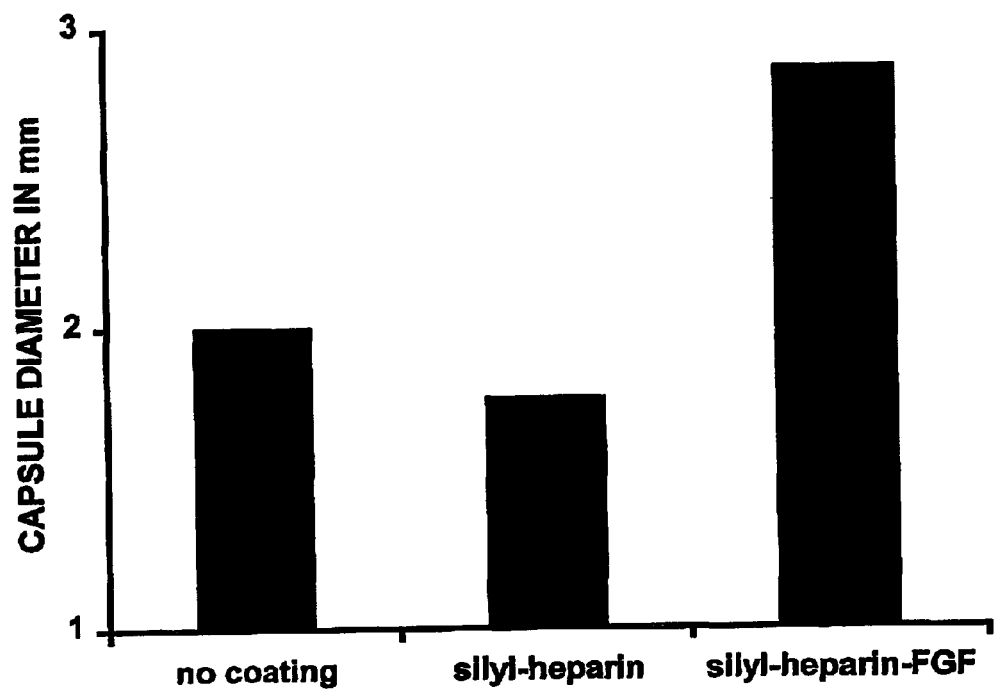
FIG. 7 is a plot, averaged from four different implants, depicting the diameter of granulation tissue surrounding suture implants with no coating, silyl-heparin, or FGF-silyl-heparin.

Vicryl suture material was coated using a solution containing silyl-heparin complex or a solution containing silyl-heparin complex followed by immersion in bFGF as described above. The suture material was then rinsed extensively, air-dried, mounted on 16 gage needles and stored until use, typically overnight. Under anesthesia, the sutures were passed through the thigh muscle of adult rats and secured with knots and surgical clips. After two weeks the animals were euthanized and the sutured area removed, fixed in formalin, and processed by standard histological methods. At two weeks, sutures coated with silyl-heparin-bFGF complex had a marked increase in cellularity in the area surrounding the implant compared to both uncoated control sutures and sutures coated with silyl-heparin complex. As shown in FIG. 7, the diameter of granulation tissue surrounding the suture coated with silyl-heparin-bFGF complex was substantially larger than either the control suture or silyl-heparin complex coated sutures. It was also observed that tissue surrounding the suture material coated with silyl-heparin complex tended to have a smaller area of granulation than that of the control suture.

EXAMPLE 21

Detection of Vascular Endothelial Growth Factor (VEGF) by Immunoassay

Figure 8:
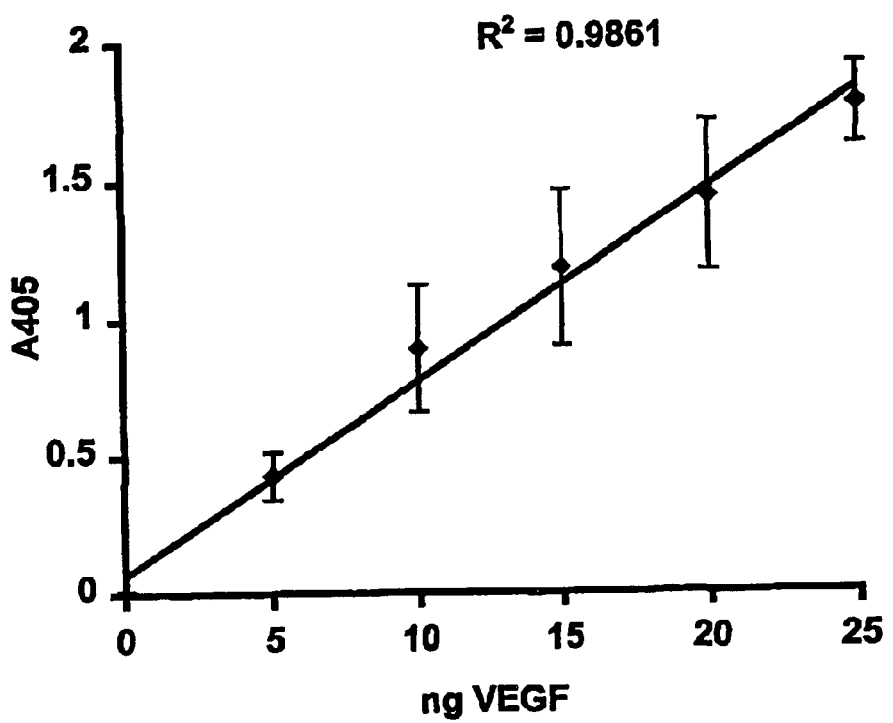
FIG. 8 is a plot of binding of vascular endothelial growth factor (VEGF) to silyl-heparin, detected using anti-VEFG antibodies.

All antibody solutions were filtered through 0.2 micron filters prior to use and prepared in phosphate buffered saline (PBS) containing 1% bovine serum albumin (BSA). Wells of 96 well polystyrene microtiter plates were coated with 30 µL of silyl heparin for 15 minutes at 37° C. The wells were rinsed extensively in water and air-dried. The wells were blocked by adding 250 µL of PBS containing 1 % BSA for 30 minutes. After removing the blocking solution, VEGF in PBS/BSA was added in 100 µL and at the appropriate concentration. The plate was incubated at 37° C. for 1 hour and rinsed 5 times in water. An aliquot of PBS/BSA con taining rabbit anti-VEGF antibodies (1:125) was added and the plate incubated for one hour. After rinsing in water, an aliquot of PBS/BSA containing horseradish peroxidase-conjugated anti-rabbit IgG (1:250) was added and incubated for one hour. After rinsing, 200 µL of chromogen (2,2'-azinobis 3-ethylbenzothiazoline-6-sulfinic acid) from a commercially available kit was added, the color developed, and the reaction stopped by adding 50 µL of aqueous 2% sodium dodecyl sulfate (SDS). The absorbance was monitored at 405 nm. The results, as shown in FIG. 8, demonstrate that VEGF bound to silyl-heparin and the binding was linear.

EXAMPLE 22

Effect of Varying "x" and "n" on Disassociation

Silyl-heparin complexes of Formula III were synthesized by varying a) the silyl chain-length in the silyl moiety ("n"), and b) the number of silyl moieties per heparin molecule ("x"). The resident time of the silyl-heparin bound to stainless steel varied, with silyl-heparin complexes where n=4 having the longest resident time. Varying the number of silyl moieties per heparin molecule, studied over the range from x=2 to x=20 also affected the resident time of the silyl-heparin complex on stainless steel, with the longest resident time observed where x=4 to x=6.

The preceding examples can be repeated with similar success by substituting the generically or specifically described reactants and/or operating conditions of this invention for those used in the preceding examples.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

What is claimed is:

1. A coating composition for contacting surfaces of medical device, said composition comprising a molecule of Formula I:

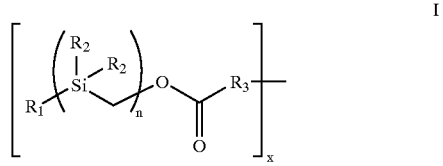

wherein
$R_1$ is an $C_{1-18}$ alkyl or $C_{6-32}$ aryl group,
each $R_2$ is independently selected from the group consisting of $C_{1-18}$ alkyl and $C_{6-32}$ aryl
$R_3$ is N or O,
n is a number from 1 to 10, and
x is a number from 1 to about 30,
bound to a heparin-activity molecule via a covalent bond, thereby forming a silyl-heparin covalent complex, with a bioactive molecule directly bound to the heparin-activity molecule.

2. The composition according to claim 1, wherein the silyl-heparin covalent complex has a disassociation rate from the contacting surface determined by the value of n and x.

3. The composition according to claim 1, wherein the silyl-heparin covalent complex binds to the contacting surfaces via hydrophobic bonding interactions.

4. The composition according to claim 3, wherein the heparin-activity molecule is heparin, heparan sulfate, hyaluronic acid, dextran, dextran sulfate, chondroitin sulfate, dermatan sulfate, or a molecule including a mixture of variably sulfated polysaccharide chains composed of repeating units of D-glucosamine and either L-iduronic or D-glucuronic acids, salts of any of the foregoing and derivatives of any of the foregoing.

5. The composition according to claim 1, wherein said bioactive molecule is directly bound to the heparin-activity molecule by affinity complexation.

6. The composition according to claim 1, wherein the silyl-heparin covalent complex comprises [benzyl-bis(dimethylsilylmethyl)]-(N-heparinyl)-carbamate or [benzyl-tris(dimethylsilylmethyl)]-(N-heparinyl)-carbamate.

7. The composition according to claim 1, wherein said bioactive molecule is an adhesive molecule, a growth factor molecule or a therapeutic molecule.

8. The composition according to claim 7, wherein the adhesive molecule is fibronectin, laminin, vitronectin, thrombospondin, gelatin, polylysine, polyornithine, peptide polymers containing adhesive sequences and heparin binding sequences, sulfated complex carbohydrates, dextran sulfate, growth hormones, cytokines, lectins, or peptidic polymers thereof.

9. The composition according to claim 7, wherein the growth factor molecule is fibroblast growth factor, platelet-derived growth factor, vascular endothelial growth factor, hepatocyte growth factor, placental growth factor, insulin-like growth factor, nerve growth factors and neurotrophins, heparin-binding epidermal growth factor, transforming growth factor-β, bone morphogenetic protein 2, osteogenic protein 1 or keratinocyte growth factor.

10. A medical device with at least one contacting surface for contacting bodily fluids, the surface having coated thereon a coating composition comprising a molecule of Formula I:

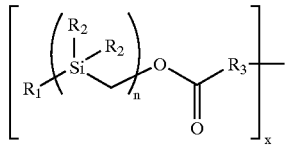

wherein
$R_1$ is an $C_{1-18}$ alkyl or $C_{6-32}$ aryl group,
each $R_2$ is independently selected from the group consisting of $C_{1-18}$ alkyl and $C_{6-32}$ aryl,
$R_3$ is N or O,
n is a number from 1 to 10, and
x is a number from 1 to about 30,
directly bound to a heparin-activity molecule via covalent bonding, thereby forming a silyl-heparin covalent complex, with a bioactive molecule directly bound to the heparin-activity molecule.

11. The device according to claim 10, wherein the silyl-heparin covalent complex binds to the surface via hydrophobic bonding interactions.

12. The device according to claim 10, wherein the silyl-heparin covalent complex has a disassociation rate from the surface determined by the value of n and x.

13. The device according to claim 10, wherein the heparin-activity molecule is heparin, heparan sulfate, hyaluronic acid, dextran, dextran sulfate, chondroitin sulfate, dermatan sulfate, or a molecule including a mixture of variably sulfated polysaccharide chains composed of repeating units of D-glucosamine and either L-iduronic or D-glucuronic acids, salts of any of the foregoing and derivatives of any of the foregoing.

14. The device according to claim 10, wherein said bioactive molecule is directly bound to the heparin-activity molecule by affinity complexation.

15. The device according to claim 10, wherein the silyl-heparin covalent complex comprises [benzyl-bis(dimethylsilylmethyl)]-(N-heparinyl)-carbamate or [benzyl-tris(dimethylsilylmethyl)]-(N-heparinyl)-carbamate.

16. The device according to claim 10, wherein the device is a blood gas exchange device, blood filter, artificial blood vessel, artificial valve, prosthetic, blood shunt, catheter, bone replacement, cartilage replacement, suture, graft, catheter or nerve growth guide.

17. The device according to claim 10, wherein said bioactive molecule is an adhesive molecule, a growth factor molecule or a therapeutic molecule.

18. The device according to claim 17, wherein the adhesive molecule is fibronectin, laminin, vitronectin, thrombospondin, gelatin, polylysine, polyornithine, peptide polymers containing adhesive sequences and heparin binding sequences, sulfated complex carbohydrates, dextran sulfate, growth hormones, cytokines, lectins, or peptidic polymers thereof.

19. The device according to claim 17, wherein the bioactive molecule is an adhesive molecule, whereby the contacting surface is non-thrombogenic and promotes cellular adhesion.

20. The device according to claim 17, wherein the growth factor molecule is fibroblast growth factor, platelet-derived growth factor, vascular endothelial growth factor, hepatocyte growth factor, placental growth factor, insulin-like growth factor, nerve growth factors and neurotrophins, heparin-binding epidermal growth factor, transforming growth factor-β, bone morphogenetic protein 2, osteogenic protein 1 or keratinocyte growth factor.

21. A method for coating a contacting surface of a medical device with a bioactive coating composition, comprising:
providing a hydrophobic silyl moiety of Formula I

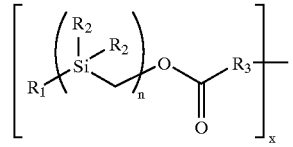

wherein
$R_1$ is an $C_{1-18}$ alkyl or $C_{6-32}$ aryl group,
each $R_2$ is independently selected from the group consisting of $C_{1-18}$ alkyl and $C_{6-32}$ aryl,
$R_3$ is N or O, and
n is a number from 1 to 10
binding said silyl moiety to a heparin-activity molecule via covalent bonding, wherein x is from 1 to about 30 for each heparin-activity molecule, thereby forming a silyl-heparin complex,
attaching the silyl-heparin complex to the contacting surface by hydrophobic interaction, and
attaching a bioactive molecule to the heparin-activity molecule.

22. The method of claim 21, wherein the silyl-heparin complex has a disassociation rate from the contacting surface determined by the value of n and x.

23. The method of claim 21, wherein the heparin-activity molecule is heparin, heparan sulfate, hyaluronic acid, dextran, dextran sulfate, chondroitin sulfate, dermatan sulfate, or a molecule including a mixture of variably sulfated polysaccharide chains composed of repeating units of D-glucosamine and either L-iduronic or D-glucuronic acids, salts of any of the foregoing and derivatives of any of the foregoing.

24. The method of claim 21, wherein the bioactive molecule is attached to the heparin-activity molecule by affinity complexation.

25. The method of claim 21, wherein the silyl-heparin complex comprises [benzyl-bis(dimethylsilylmethyl)]-(N-heparinyl)-carbamate or [benzyl-tris(dimethylsilylmethyl)]-(N-heparinyl)-carbamate.

26. The method of claim 21, wherein the bioactive molecule is an adhesive molecule, whereby the contacting surface is non-thrombogenic and promotes cellular adhesion.

27. The method of claim 21, wherein the bioactive molecule is an adhesive molecule, a growth factor molecule or a therapeutic molecule.

28. The method of claim 27, wherein the adhesive molecule is fibronectin, laminin, vitronectin, thrombospondin, gelatin, polylysine, polyornithine, peptide polymers containing adhesive sequences and heparin binding sequences, sulfated complex carbohydrates, dextran sulfate, growth hormones, cytokines, lectins, or peptidic polymers thereof.

29. The method of claim 27, wherein the growth factor molecule is fibroblast growth factor, platelet-derived growth factor, vascular endothelial growth factor, hepatocyte growth factor, placental growth factor, insulin-like growth factor, nerve growth factors and neurotrophins, heparin-binding epidermal growth factor, transforming growth factor-$\beta$, bone morphogenetic protein 2, osteogenic protein 1 or keratinocyte growth factor.

* * * * *

SEQUENCE LISTING

```
<160> NUMBER OF SEQ ID NOS: 2

<210> SEQ ID NO 1
<211> LENGTH: 5
<212> TYPE: PRT
<213> ORGANISM: Artificial
<220> FEATURE:
<223> OTHER INFORMATION: laminin basement membrane derived peptide

<400> SEQUENCE: 1

Ile Lys Val Ala Val
1               5

<210> SEQ ID NO 2
<211> LENGTH: 5
<212> TYPE: PRT
<213> ORGANISM: Artificial
<220> FEATURE:
<223> OTHER INFORMATION: laminin basement membrane derived peptide

<400> SEQUENCE: 2

Tyr Ile Gly Ser Arg
1               5
```